United States Patent
Vivenzio et al.

(10) Patent No.: US 8,142,352 B2
(45) Date of Patent: Mar. 27, 2012

(54) VAGINAL SPECULUM ASSEMBLY HAVING PORTABLE ILLUMINATOR

(75) Inventors: Robert L. Vivenzio, Auburn, NY (US); Michael T. McMahon, Syracuse, NY (US); Steven R. Slawson, Camillus, NY (US); Dominick Danna, Syracuse, NY (US); Allan I. Krauter, Skaneateles, NY (US); Dale C. Saddlemire, Cortland, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 138 days.

(21) Appl. No.: 11/731,631

(22) Filed: Mar. 30, 2007

(65) Prior Publication Data

US 2007/0230164 A1    Oct. 4, 2007

Related U.S. Application Data

(63) Continuation-in-part of application No. PCT/US2006/012116, filed on Apr. 3, 2006, and a continuation-in-part of application No. PCT/US2006/012320, filed on Apr. 3, 2006, and a continuation-in-part of application No. PCT/US2006/012322, filed on Apr. 3, 2006.

(60) Provisional application No. 60/876,346, filed on Dec. 21, 2006.

(51) Int. Cl.
*A61B 1/267* (2006.01)

(52) U.S. Cl. ......... 600/199; 600/186; 600/223; 600/245

(58) Field of Classification Search .......... 600/201–204, 600/212, 223, 241, 245, 284–246; 362/109, 362/114, 119
See application file for complete search history.

(56) References Cited

U.S. PATENT DOCUMENTS

| | | | |
|---|---|---|---|
| 553,728 A | 1/1896 | Campbell |
| 3,592,199 A | 7/1971 | Ostensen |
| 3,716,047 A | 2/1973 | Moore |
| 3,789,835 A | 2/1974 | Whitman |
| 3,885,211 A | 5/1975 | Gutai |
| 3,890,961 A | 6/1975 | Moore et al. |
| 3,934,578 A | 1/1976 | Heine et al. |
| 3,945,371 A | 3/1976 | Adelman et al. |
| 3,978,850 A | 9/1976 | Moore et al. |
| 3,985,125 A | 10/1976 | Rose et al. |
| 3,994,288 A | 11/1976 | Stumpf |
| 4,010,740 A | 3/1977 | Littorin et al. |
| 245,515 A | 8/1977 | Troutner et al. |
| D245,515 S | 8/1977 | Troutner et al. |
| 4,067,323 A | 1/1978 | Troutner et al. |

(Continued)

FOREIGN PATENT DOCUMENTS

CN    2053088 U    2/1990

(Continued)

OTHER PUBLICATIONS

International Search Report/Written Opinion (ISR/WO), Jun. 5, 2008, 7 pages.

(Continued)

*Primary Examiner* — Eduardo C Robert
*Assistant Examiner* — Christina Negrelli

(57) ABSTRACT

A portable illuminator includes a contained power source and an integrally contained light source that is selectively inserted into the handle portion of a vaginal speculum. The portable illuminator includes at least one feature to protect the illuminator from contamination and to prevent users from pinching or snagging gloves or fingers during operation.

38 Claims, 10 Drawing Sheets

U.S. PATENT DOCUMENTS

| | | | |
|---|---|---|---|
| 4,091,807 A | 5/1978 | Dickinson, III et al. |
| 4,156,424 A | 5/1979 | Burgin |
| 4,202,324 A | 5/1980 | Alison |
| 4,210,133 A | 7/1980 | Castaneda et al. |
| 4,220,985 A | 9/1980 | Hukuba |
| 4,227,537 A | 10/1980 | Suciu et al. |
| 4,244,357 A | 1/1981 | Morrison |
| 4,263,898 A | 4/1981 | Wannag et al. |
| 4,263,899 A | 4/1981 | Burgin |
| 4,300,541 A | 11/1981 | Burgin |
| 4,337,763 A | 7/1982 | Petrassevich |
| 4,377,157 A | 3/1983 | Zartman |
| 4,432,351 A | 2/1984 | Hoary et al. |
| D274,356 S | 6/1984 | Riedell |
| 4,492,220 A | 1/1985 | Hayes |
| 4,502,468 A | 3/1985 | Burgin |
| 4,517,628 A | 5/1985 | McDermott |
| 4,517,702 A | 5/1985 | Jackson |
| 4,542,741 A | 9/1985 | Burgin |
| 4,546,761 A | 10/1985 | McCullough |
| 4,556,052 A | 12/1985 | Muller et al. |
| 4,562,832 A | 1/1986 | Wilder et al. |
| 4,566,439 A | 1/1986 | Burgin |
| 4,576,168 A | 3/1986 | Jalowayski |
| 4,597,383 A | 7/1986 | VanDerBel |
| 4,607,623 A | 8/1986 | Bauman |
| 4,619,248 A | 10/1986 | Walsh et al. |
| RE32,275 E | 11/1986 | Zartman |
| 4,638,792 A | 1/1987 | Burgin |
| 4,641,663 A | 2/1987 | Juhn |
| 4,643,172 A * | 2/1987 | Taff et al. ............... 600/203 |
| 4,646,722 A | 3/1987 | Silverstein et al. |
| 4,657,012 A | 4/1987 | Burgin |
| 4,741,326 A | 5/1988 | Sidall et al. |
| 4,763,678 A | 8/1988 | Ott |
| 4,766,886 A | 8/1988 | Juhn |
| 4,766,887 A | 8/1988 | Cecil, Jr. et al. |
| 4,790,751 A | 12/1988 | Reinhardt et al. |
| 299,532 A | 1/1989 | Cecil, Jr. et al. |
| D299,532 S | 1/1989 | Cecil, Jr. et al. |
| 4,800,896 A | 1/1989 | Jalowayski |
| 4,807,599 A * | 2/1989 | Robinson et al. ............ 600/212 |
| 4,807,600 A | 2/1989 | Hayes |
| 4,811,937 A | 3/1989 | Rothman |
| 4,825,850 A | 5/1989 | Opie et al. |
| 4,854,300 A | 8/1989 | Corbo et al. |
| 4,867,177 A | 9/1989 | Urheim |
| 4,869,238 A | 9/1989 | Opie et al. |
| 4,872,837 A | 10/1989 | Issalene et al. |
| 4,884,559 A | 12/1989 | Collins |
| 4,905,670 A | 3/1990 | Adair |
| 4,971,036 A | 11/1990 | Collins |
| 4,979,498 A | 12/1990 | Oneda et al. |
| 4,981,086 A | 1/1991 | Barca et al. |
| 4,994,070 A | 2/1991 | Waters et al. |
| 5,007,409 A | 4/1991 | Pope |
| 5,018,507 A | 5/1991 | Montaldi |
| 5,026,368 A | 6/1991 | Adair |
| 5,052,372 A | 10/1991 | Shapiro |
| 5,054,906 A | 10/1991 | Lyons, Jr. |
| 5,063,908 A | 11/1991 | Collins |
| 5,067,491 A | 11/1991 | Taylor, II et al. |
| 5,072,720 A | 12/1991 | Francis et al. |
| 5,081,983 A | 1/1992 | Villalta et al. |
| 5,143,054 A | 9/1992 | Adair |
| 34,110 A | 10/1992 | Opie |
| RE34,110 E | 10/1992 | Opie et al. |
| 5,165,387 A | 11/1992 | Woodson |
| 5,174,278 A | 12/1992 | Babkow |
| 5,179,937 A | 1/1993 | Lee et al. |
| 5,179,938 A | 1/1993 | Lonky |
| 5,186,180 A | 2/1993 | Bellas et al. |
| 5,201,908 A | 4/1993 | Jones |
| 5,222,271 A | 6/1993 | Eganhouse |
| 5,231,973 A | 8/1993 | Dickie et al. |
| 5,243,966 A | 9/1993 | Ng |
| 5,250,065 A | 10/1993 | Clement et al. |
| 5,284,474 A | 2/1994 | Adair |
| 5,306,237 A | 4/1994 | Clement et al. |
| 5,318,010 A | 6/1994 | Lundberg et al. |
| 5,329,937 A | 7/1994 | Krstevich et al. |
| 5,329,938 A | 7/1994 | Lonky |
| 5,337,734 A | 8/1994 | Saab |
| 5,338,292 A | 8/1994 | Clement et al. |
| 5,349,941 A | 9/1994 | Hori |
| 5,374,244 A | 12/1994 | Clement et al. |
| 5,377,667 A | 1/1995 | Patton et al. |
| 5,386,817 A | 2/1995 | Jones |
| 5,390,663 A | 2/1995 | Schaefer |
| 5,392,764 A | 2/1995 | Swanson et al. |
| 5,394,863 A | 3/1995 | Sanford et al. |
| 5,395,354 A | 3/1995 | Vancaillie |
| 5,433,190 A | 7/1995 | Sunalp |
| 5,450,857 A | 9/1995 | Garfield et al. |
| 5,458,132 A | 10/1995 | Yabe et al. |
| 5,458,595 A | 10/1995 | Tadir et al. |
| 5,460,165 A | 10/1995 | Mayes |
| 5,465,709 A | 11/1995 | Dickie et al. |
| 5,472,345 A | 12/1995 | Eggert |
| 5,499,964 A | 3/1996 | Beck et al. |
| 5,505,690 A | 4/1996 | Patton et al. |
| 5,509,893 A | 4/1996 | Pracas et al. |
| 5,595,344 A | 1/1997 | Starnes |
| 5,639,238 A | 6/1997 | Fishburne, Jr. |
| 5,656,014 A | 8/1997 | Rooney et al. |
| 5,695,492 A | 12/1997 | Brown |
| 5,704,901 A | 1/1998 | Meister |
| 5,709,221 A | 1/1998 | Vancaillie et al. |
| 5,711,921 A | 1/1998 | Langford |
| 5,716,329 A | 2/1998 | Dieter |
| 5,718,665 A | 2/1998 | Stubbs |
| 5,722,983 A | 3/1998 | Van Der Weegen et al. |
| 5,743,852 A | 4/1998 | Johnson |
| 5,746,694 A | 5/1998 | Wilk et al. |
| 5,762,605 A | 6/1998 | Cane et al. |
| 5,772,435 A | 6/1998 | Dorman |
| 5,785,648 A | 7/1998 | Min |
| 5,787,891 A | 8/1998 | Sak |
| 5,795,289 A | 8/1998 | Wyttenbach |
| 5,799,126 A | 8/1998 | Nagatani et al. |
| 5,800,350 A | 9/1998 | Coppleson et al. |
| 5,836,764 A | 11/1998 | Buchanan |
| 5,840,012 A | 11/1998 | Krauter et al. |
| 5,842,974 A | 12/1998 | Stubbs |
| 5,846,249 A | 12/1998 | Thompson |
| 5,865,729 A | 2/1999 | Meehan et al. |
| 5,868,668 A | 2/1999 | Weiss |
| 5,873,820 A | 2/1999 | Norell et al. |
| 5,879,286 A | 3/1999 | Krauter et al. |
| 5,899,854 A | 5/1999 | Slishman |
| 5,902,314 A | 5/1999 | Koch |
| 5,906,802 A | 5/1999 | Langford |
| 5,916,150 A | 6/1999 | Sillman |
| 5,916,151 A | 6/1999 | Charters et al. |
| 5,921,777 A | 7/1999 | Dorman |
| 5,931,776 A | 8/1999 | Dotolo |
| 5,934,904 A | 8/1999 | Elrod et al. |
| 5,941,822 A | 8/1999 | Skladnev et al. |
| 5,941,834 A | 8/1999 | Skladnev et al. |
| 5,941,873 A | 8/1999 | Korenfeld |
| 5,961,937 A | 10/1999 | Gobbato et al. |
| 5,997,474 A | 12/1999 | Batchelor et al. |
| 6,004,265 A | 12/1999 | Hsu et al. |
| 6,024,696 A | 2/2000 | Hoftman et al. |
| 6,024,697 A | 2/2000 | Pisarik |
| 6,026,323 A | 2/2000 | Skladnev et al. |
| 6,030,210 A | 2/2000 | Bianchetti et al. |
| 6,031,036 A | 2/2000 | Rosenquist et al. |
| 6,036,638 A | 3/2000 | Nwawka |
| 6,048,308 A | 4/2000 | Strong |
| 6,068,593 A | 5/2000 | Krauter et al. |
| 6,074,405 A | 6/2000 | Koch |
| 6,077,216 A | 6/2000 | Benderev et al. |
| 6,095,810 A | 8/2000 | Bianchetti et al. |
| 6,096,046 A | 8/2000 | Weiss |
| 6,117,090 A | 9/2000 | Caillouette |
| 6,117,285 A | 9/2000 | Welch et al. |

| | | | | | | |
|---|---|---|---|---|---|---|
| 6,130,520 | A | 10/2000 | Wawro et al. | 6,802,817 B2 | 10/2004 | Baxter-Jones et al. |
| 6,143,512 | A | 11/2000 | Markovic et al. | 6,804,930 B2 | 10/2004 | Stravitz |
| 6,155,990 | A | 12/2000 | Fournier | 6,807,681 B2 | 10/2004 | Sorrels |
| 6,159,162 | A | 12/2000 | Kostylev et al. | 6,830,547 B2 | 12/2004 | Weiss |
| 6,176,824 | B1 | 1/2001 | Davis | 6,848,796 B2 | 2/2005 | Tagirov et al. |
| 6,179,614 | B1 | 1/2001 | Elrod et al. | 6,863,674 B2 | 3/2005 | Kasahara et al. |
| 6,186,944 | B1 | 2/2001 | Tsai | 6,869,398 B2 | 3/2005 | Obenchain et al. |
| 6,206,839 | B1 | 3/2001 | Zwelling-Aamot | 6,889,400 B2 | 5/2005 | Kawazoe et al. |
| 6,217,512 | B1 | 4/2001 | Salo et al. | 6,889,832 B2 | 5/2005 | Gabele et al. |
| 6,258,024 | B1 | 7/2001 | van Der Weegen et al. | 6,895,965 B2 | 5/2005 | Scarberry et al. |
| 6,267,752 | B1 | 7/2001 | Svetliza et al. | 6,896,653 B1 | 5/2005 | Vail, III et al. |
| 6,277,067 | B1 | 8/2001 | Blair | 6,898,012 B2 | 5/2005 | Kaminsky et al. |
| 6,280,379 | B1 | 8/2001 | Resnick | 6,898,819 B2 | 5/2005 | Tanaka et al. |
| 6,302,853 | B1 | 10/2001 | Sak | 6,902,278 B2 | 6/2005 | Bala |
| 6,306,084 | B1 | 10/2001 | Pinczower | 6,908,428 B2 | 6/2005 | Aizenfeld et al. |
| 6,319,199 | B1 | 11/2001 | Sheehan et al. | 6,926,677 B2 | 8/2005 | Richards |
| 6,342,036 | B1 | 1/2002 | Cooper et al. | 6,929,601 B2 | 8/2005 | Nakao |
| 6,346,085 | B1 | 2/2002 | Schiffman | 6,936,013 B2 | 8/2005 | Pevoto |
| 6,354,995 | B1 | 3/2002 | Hoftman et al. | 6,957,897 B1 | 10/2005 | Nelson et al. |
| 6,361,489 | B1 | 3/2002 | Tsai | 6,970,238 B2 | 11/2005 | Gerhard et al. |
| 6,364,832 | B1 | 4/2002 | Propp | 6,974,294 B2 | 12/2005 | Pressman et al. |
| 6,371,973 | B1 | 4/2002 | Tepper et al. | 6,986,686 B2 | 1/2006 | Shibata et al. |
| 6,379,296 | B1 | 4/2002 | Baggett | 7,014,340 B2 | 3/2006 | Bettis |
| 6,379,299 | B1 | 4/2002 | Borodulin et al. | 7,018,592 B2 | 3/2006 | Bowen |
| 6,379,315 | B1 | 4/2002 | Claren et al. | 7,021,798 B2 | 4/2006 | Tsimerman et al. |
| 6,394,111 | B1 | 5/2002 | Jacobs et al. | 7,041,056 B2 | 5/2006 | Deslauriers et al. |
| 6,394,950 | B1 | 5/2002 | Weiss | 7,041,248 B2 | 5/2006 | Van Der Weegen et al. |
| 6,397,847 | B1 | 6/2002 | Scarberry et al. | 7,048,744 B2 | 5/2006 | Wiess |
| 6,416,321 | B2 | 7/2002 | Gugel et al. | 7,056,293 B2 | 6/2006 | Reeves et al. |
| 6,416,467 | B1 | 7/2002 | McMillin et al. | 7,060,039 B2 | 6/2006 | Voegele |
| 6,419,646 | B1 | 7/2002 | Baxter-Jones | 7,081,090 B2 | 7/2006 | Strong et al. |
| 6,432,048 | B1 | 8/2002 | Francois | 7,081,097 B2 | 7/2006 | Martone et al. |
| 6,432,049 | B1 * | 8/2002 | Banta et al. ............ 600/249 | 7,086,859 B2 | 8/2006 | Gregorio et al. |
| 6,436,033 | B2 | 8/2002 | Tan | 7,087,028 B2 | 8/2006 | Sak |
| 6,450,952 | B1 | 9/2002 | Rioux et al. | 7,127,771 B2 | 10/2006 | McDevitt et al. |
| 6,450,977 | B1 | 9/2002 | Baxter-Jones | 7,141,015 B2 | 11/2006 | Ruane |
| 6,454,874 | B1 | 9/2002 | Jacobs et al. | 7,179,087 B2 | 2/2007 | Kuhn et al. |
| 6,468,232 | B1 | 10/2002 | Ashton-Miller et al. | 7,194,301 B2 | 3/2007 | Jenkins et al. |
| 6,475,164 | B2 | 11/2002 | Gombrich et al. | 7,232,230 B2 | 6/2007 | Bala |
| 6,475,165 | B1 | 11/2002 | Fournier | 2001/0029044 A1 | 10/2001 | Gombrich et al. |
| 6,485,410 | B1 | 11/2002 | Loy | 2001/0029387 A1 | 10/2001 | Wolf et al. |
| 6,487,440 | B2 | 11/2002 | Deckert et al. | 2001/0033805 A1 | 10/2001 | Jacobs et al. |
| 6,494,964 | B1 | 12/2002 | Jacobs et al. | 2001/0034917 A1 | 11/2001 | DuCey |
| 6,496,718 | B1 | 12/2002 | Lonky | 2002/0016525 A1 | 2/2002 | Ishibiki |
| 6,514,198 | B2 | 2/2003 | Ishibiki et al. | 2002/0022769 A1 | 2/2002 | Smith et al. |
| 6,516,817 | B2 | 2/2003 | Jacobs et al. | 2002/0026157 A1 | 2/2002 | Fournier |
| 6,516,818 | B2 | 2/2003 | Jacobs et al. | 2002/0038075 A1 | 3/2002 | Tsai |
| 6,524,259 | B2 | 2/2003 | Baxter-Jones et al. | 2002/0038076 A1 | 3/2002 | Sheehan et al. |
| 6,537,285 | B1 | 3/2003 | Hatasaka, Jr. et al. | 2002/0055670 A1 | 5/2002 | Weiss |
| 6,558,381 | B2 | 5/2003 | Ingle et al. | 2002/0058230 A1 | 5/2002 | Savin et al. |
| 6,569,091 | B2 | 5/2003 | Diokno et al. | 2002/0119419 A1 | 8/2002 | Suzuki et al. |
| 6,585,727 | B1 | 7/2003 | Cashman et al. | 2002/0120210 A1 | 8/2002 | Voegele |
| 6,589,168 | B2 | 7/2003 | Thompson | 2002/0137006 A1 | 9/2002 | Gugel et al. |
| 6,595,917 | B2 | 7/2003 | Nieto | 2002/0137008 A1 | 9/2002 | McSpadden et al. |
| 6,610,020 | B2 | 8/2003 | Voegele | 2002/0156350 A1 | 10/2002 | Nieto |
| 6,612,099 | B2 | 9/2003 | Stravitz | 2002/0156395 A1 | 10/2002 | Stephens et al. |
| 6,620,111 | B2 | 9/2003 | Stephens et al. | 2002/0162304 A1 | 11/2002 | Stravitz |
| 6,626,825 | B2 | 9/2003 | Tsai | 2002/0165433 A1 | 11/2002 | Stihl |
| 6,626,826 | B1 | 9/2003 | Van Der Weegen et al. | 2002/0165435 A1 | 11/2002 | Weiss |
| 6,629,535 | B2 | 10/2003 | Ingle et al. | 2002/0170133 A1 | 11/2002 | McDevitt et al. |
| 6,652,453 | B2 | 11/2003 | Smith et al. | 2002/0198471 A1 | 12/2002 | Baxter-Jones et al. |
| 6,663,576 | B2 | 12/2003 | Gombrich et al. | 2003/0083547 A1 | 5/2003 | Hamilton et al. |
| 6,669,654 | B2 | 12/2003 | Diokno et al. | 2003/0114803 A1 | 6/2003 | Lerner |
| 6,702,740 | B2 | 3/2004 | Herold | 2003/0125666 A1 | 7/2003 | Kasahara et al. |
| 6,702,741 | B2 | 3/2004 | Rioux et al. | 2003/0134255 A1 | 7/2003 | Masterman et al. |
| 6,702,759 | B2 | 3/2004 | Pevoto | 2003/0139673 A1 | 7/2003 | Vivenzio et al. |
| 6,712,761 | B2 | 3/2004 | Borodulin et al. | 2003/0158502 A1 | 8/2003 | Baxter-Jones et al. |
| 6,719,561 | B2 | 4/2004 | Gugel et al. | 2003/0164182 A1 | 9/2003 | Jacobs et al. |
| 6,719,687 | B1 | 4/2004 | Van Der Weegen et al. | 2003/0176772 A1 | 9/2003 | Yang |
| 6,721,987 | B2 | 4/2004 | McDevitt et al. | 2003/0187331 A1 | 10/2003 | Faludi et al. |
| 6,730,085 | B2 | 5/2004 | George et al. | 2003/0188761 A1 | 10/2003 | Garcia et al. |
| 6,739,744 | B2 | 5/2004 | Williams et al. | 2003/0195434 A1 | 10/2003 | Voegele |
| 6,740,049 | B2 | 5/2004 | Wallach | 2003/0208995 A1 | 11/2003 | Stravitz |
| 6,743,198 | B1 | 6/2004 | Tihon | 2003/0213074 A1 | 11/2003 | Kawazoe et al. |
| 6,749,563 | B2 | 6/2004 | Stihl et al. | 2003/0213082 A1 | 11/2003 | Tanaka |
| 6,752,629 | B2 | 6/2004 | Suzuki et al. | 2004/0014000 A1 | 1/2004 | Bernhard |
| 6,761,687 | B1 | 7/2004 | Doshi et al. | 2004/0026829 A1 | 2/2004 | Van Der Weegen |
| 6,793,661 | B2 | 9/2004 | Hamilton et al. | 2004/0054260 A1 | 3/2004 | Klaassen et al. |
| 6,800,859 | B1 | 10/2004 | Shishido et al. | 2004/0059253 A1 | 3/2004 | Martone et al. |

| | | |
|---|---|---|
| 2004/0064053 A1 | 4/2004 | Chang et al. |
| 2004/0076019 A1 | 4/2004 | Tsimerman et al. |
| 2004/0083681 A1 | 5/2004 | Stravitz |
| 2004/0084058 A1 | 5/2004 | Tyndal |
| 2004/0084070 A1 | 5/2004 | Sasaki et al. |
| 2004/0118440 A1 | 6/2004 | Sasaki et al. |
| 2004/0141175 A1 | 7/2004 | Baldwin et al. |
| 2004/0153116 A1 | 8/2004 | Nobles et al. |
| 2004/0166474 A1 | 8/2004 | Gugel et al. |
| 2004/0183482 A1 | 9/2004 | Roberts et al. |
| 2004/0184288 A1 | 9/2004 | Bettis |
| 2004/0186355 A1* | 9/2004 | Strong et al. .......... 600/220 |
| 2004/0190140 A1 | 9/2004 | Bala |
| 2004/0191723 A1 | 9/2004 | Shearer et al. |
| 2004/0193104 A1 | 9/2004 | Jervis |
| 2004/0209237 A1 | 10/2004 | Flewelling et al. |
| 2004/0214156 A1 | 10/2004 | Schomacker et al. |
| 2004/0220478 A1 | 11/2004 | Wallace et al. |
| 2004/0225267 A1 | 11/2004 | Tapadiya |
| 2005/0021017 A1 | 1/2005 | Karasawa et al. |
| 2005/0021069 A1 | 1/2005 | Feuer et al. |
| 2005/0021080 A1 | 1/2005 | Feuer et al. |
| 2005/0033119 A1 | 2/2005 | Okawa et al. |
| 2005/0043588 A1 | 2/2005 | Tsai |
| 2005/0054894 A1 | 3/2005 | Aizenfeld et al. |
| 2005/0065496 A1 | 3/2005 | Simon et al. |
| 2005/0071938 A1 | 4/2005 | McDevitt et al. |
| 2005/0080462 A1 | 4/2005 | Jenkins et al. |
| 2005/0085699 A1 | 4/2005 | Weiss |
| 2005/0125027 A1 | 6/2005 | Knodel et al. |
| 2005/0137613 A1 | 6/2005 | Kasahara et al. |
| 2005/0148819 A1 | 7/2005 | Noguchi et al. |
| 2005/0159752 A1 | 7/2005 | Walker et al. |
| 2005/0162028 A1 | 7/2005 | Kardeis et al. |
| 2005/0192482 A1 | 9/2005 | Carpenter et al. |
| 2005/0209507 A1 | 9/2005 | Suzuki et al. |
| 2005/0214881 A1 | 9/2005 | Azarnia et al. |
| 2005/0215858 A1 | 9/2005 | Vail |
| 2005/0222601 A1 | 10/2005 | Erhard |
| 2005/0236230 A1 | 10/2005 | Fee |
| 2005/0261763 A1 | 11/2005 | Wang et al. |
| 2005/0274093 A1 | 12/2005 | Stravitz et al. |
| 2005/0278020 A1 | 12/2005 | Wang et al. |
| 2005/0282112 A1 | 12/2005 | Kumar |
| 2005/0286130 A1 | 12/2005 | Bala |
| 2006/0004271 A1 | 1/2006 | Peyser et al. |
| 2006/0027246 A1 | 2/2006 | Wilkinson |
| 2006/0029901 A1 | 2/2006 | Rose et al. |
| 2006/0037165 A1 | 2/2006 | McDevitt et al. |
| 2006/0041274 A1 | 2/2006 | Su |
| 2006/0046226 A1 | 3/2006 | Bergler et al. |
| 2006/0084843 A1 | 4/2006 | Sommerich et al. |
| 2006/0085932 A1 | 4/2006 | Santos |
| 2006/0089529 A1 | 4/2006 | Tartaglia et al. |
| 2006/0104856 A1 | 5/2006 | Farrell et al. |
| 2006/0110700 A1 | 5/2006 | Cipolla et al. |
| 2006/0116551 A1 | 6/2006 | Lovett et al. |
| 2006/0127844 A1 | 6/2006 | Michaelian |
| 2006/0130438 A1 | 6/2006 | Stravitz et al. |
| 2006/0137122 A1 | 6/2006 | Ryan |

FOREIGN PATENT DOCUMENTS

| | | |
|---|---|---|
| CN | 2387854 Y | 7/2000 |
| WO | WO 2004/037287 | 5/2004 |
| WO | WO 2006/107877 A2 | 10/2006 |
| WO | WO 2006/121530 A2 | 11/2006 |

OTHER PUBLICATIONS

Supplementary European Search Report for EP Application No. 06 749 169.6; mailed May 8, 2009; 9 pages.

Supplementary European Search Report for EP Application No. 06 749 170.4; mailed May 8, 2009; 13 pages.

Foreign Office Action for CN Application No. 200680017514.1; 16 pages.

European Office Action for EP Application No. 06 749 170.4; dated Jan. 17, 2011; 4 pages.

* cited by examiner

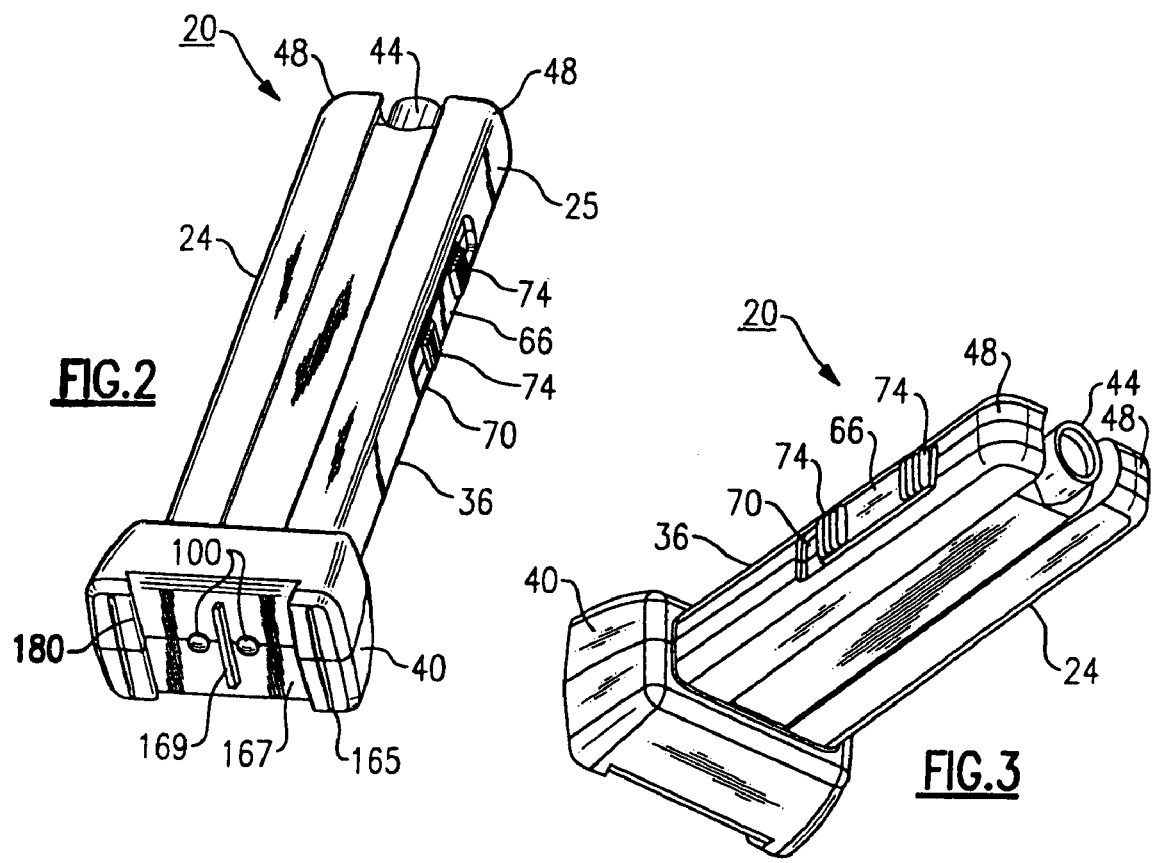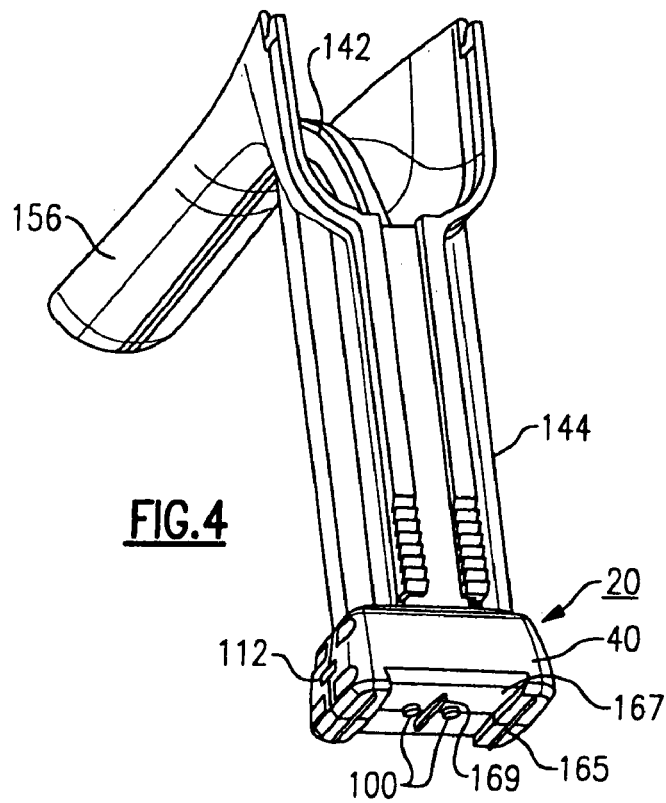

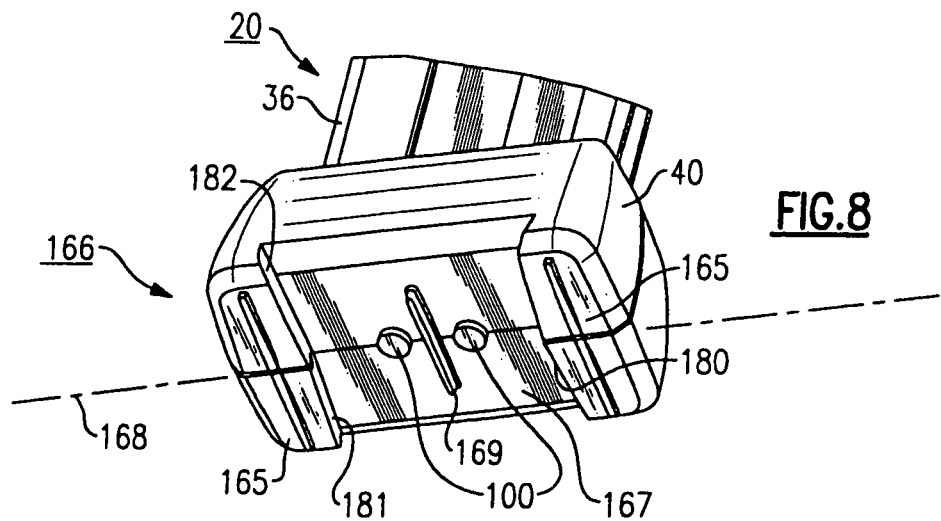
FIG.8
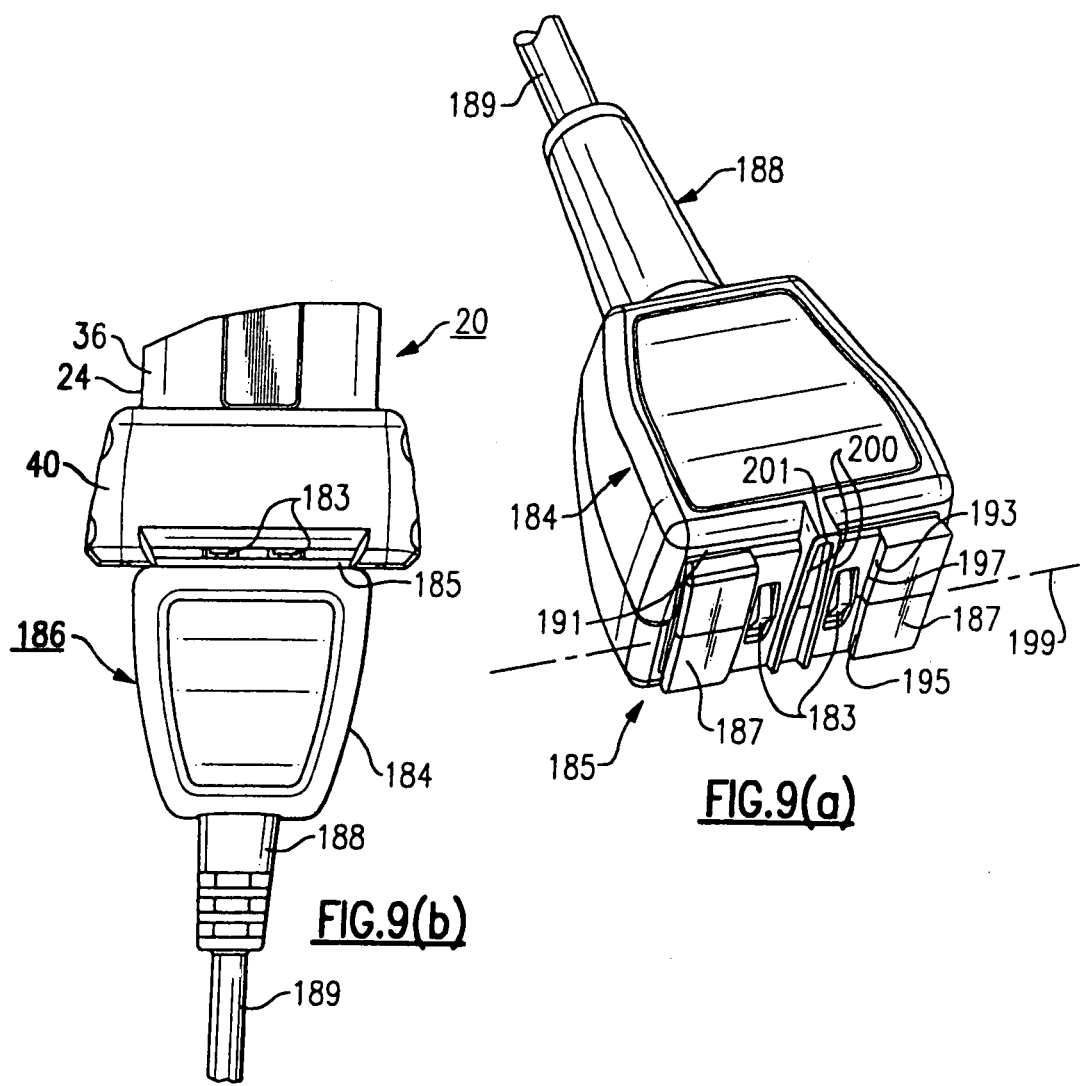
FIG.9(a)
FIG.9(b)

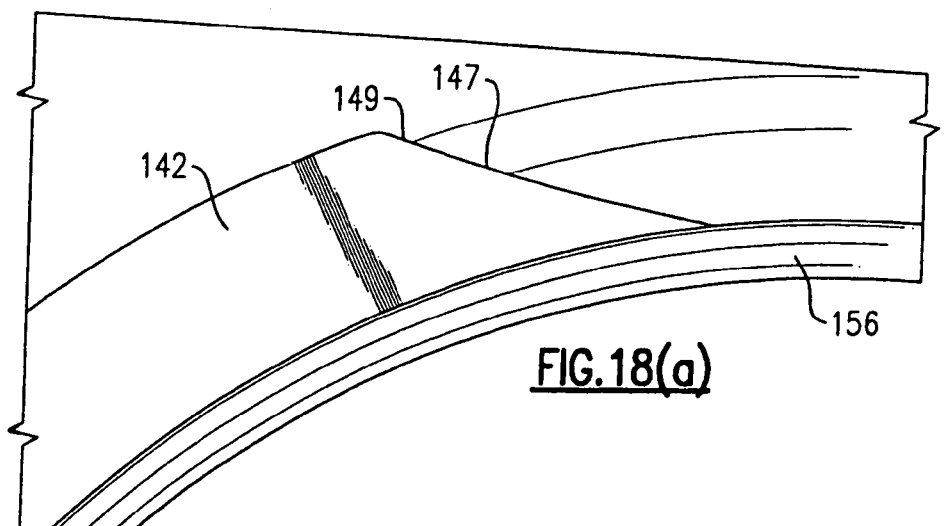
FIG.18(a)
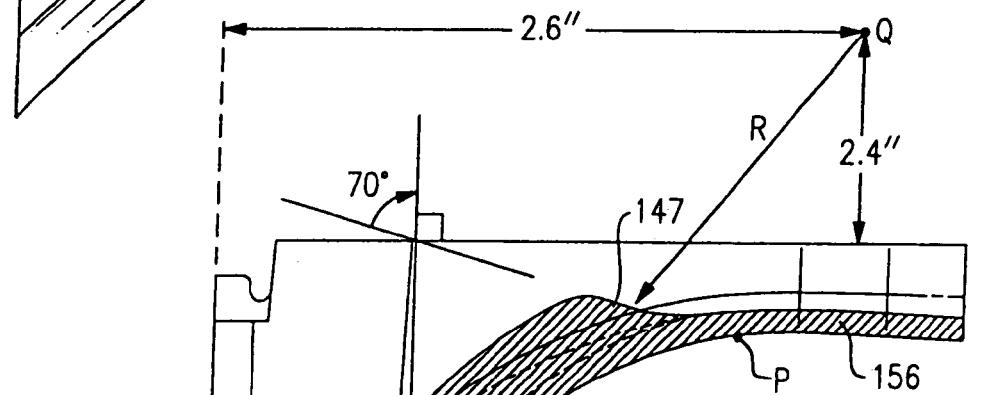
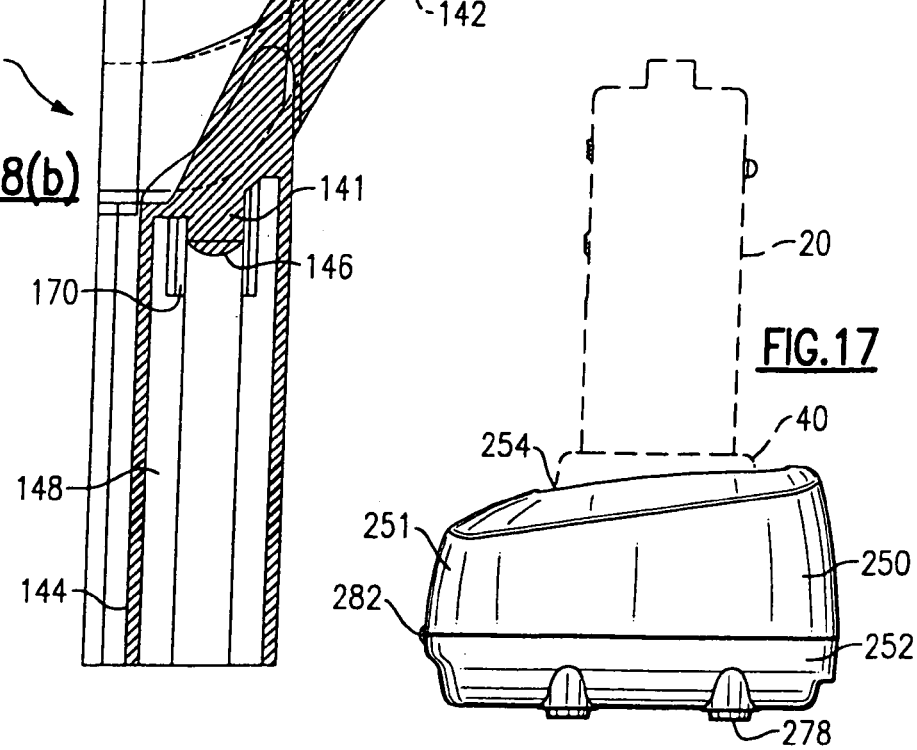
FIG.18(b)
FIG.17

VAGINAL SPECULUM ASSEMBLY HAVING PORTABLE ILLUMINATOR

CROSS REFERENCE TO RELATED APPLICATIONS

This application is a nonprovisional application filed under 35 U.S.C. §119 and based upon U.S. Ser. No. 60/876,346, filed Dec. 21, 2006. This application is also a continuation in part (CIP) application filed under 35 U.S.C.§120 of PCT PCT/US2006/12116, filed Apr. 3, 2006, PCT/US2006/12320, filed Apr. 3, 2006, and PCT/US2006/012322, filed Apr. 3, 2006. This application also further relates to commonly assigned and concurrently filed U.S. Ser. No. 11/731,189, filed Mar. 30, 2007, (U.S. Pat. No. 7,758,203), the entire contents of each of the preceding documents being incorporated by reference herein.

FIELD OF THE INVENTION

The invention relates to the field of diagnostic medical devices and in particular to a portable illuminator as used in conjunction with a disposable vaginal speculum, independently as an examination light, or in conjunction with other medical devices.

BACKGROUND OF THE INVENTION

Presently, vaginal specula are used in the diagnostic medical field to examine the cervix of a female patient. A number of various specula designs have been developed, including disposable plastic versions that are designed for single use or single patient use. Applicant has previously developed a line of disposable plastic vaginal specula that are defined by an upper blade and a lower blade, the latter including a pistol-grip like handle portion having a receiving cavity that is sized to retain an illumination assembly. The handle portion further includes a curved light pipe disposed in the upper end of the handle portion and along the lower blade wherein light from the illumination assembly is directed towards the target. The illumination assembly includes a housing containing a miniature light source, such as a miniature incandescent lamp, which is tethered by means of a cable to a power source, such as a wall transformer. The user grips the handle portion having the inserted illumination assembly and views the cervix after the blades have been opened in the patient through articulation of the blades. The cervix is viewed through an aperture formed in the proximal end of the speculum. The speculum is discarded after use, but the illumination assembly is reusable between patients.

A number of problems have been discovered in the use and maintenance of such apparatus. For example, the use of a tethered illumination assembly that requires an AC or similar power source is often inconvenient in the field, particularly remote areas in which access to such a power supply is uncertain. In addition, the use of a tethered illumination assembly presents access and other issues, for example, with bed-ridden patients. There are similar concerns relating to the use of incandescent lamps as a light source in that such sources are typically sealed within the housing of the illumination assembly and are subject to breakage, for example, if the illumination assembly is dropped. Incandescent lamps produce significant heat, which is a concern to both the caregiver and the patient, and have a finite service life, requiring periodic tear-down or replacement of the entire illumination assembly. In addition, incandescent lamps are relatively expensive, as compared, for example, with other types of commercially available light sources, thereby impacting the cost of such apparatus.

In the utilization of alternative light sources, one concern that becomes more important is insuring that adequate alignment is realized between the light source and the curved light pipe. Lack of sufficient optical coupling between these components would result in inadequate or inconsistent illumination and light spot quality.

Another encountered problem relates to cleaning of illumination assemblies between patient examinations. The nature of a cervical examination includes the presence of bodily fluids, requiring the caregiver to wear gloves in handling the apparatus to avoid cross contamination. Though the speculum is a disposable component, there is a need to clean the reusable illuminator between patient examinations. In addition, there is a further tendency for the user to pinch or snag his or her glove or fingers during operation using the above apparatus, either in fitting the illumination assembly within the speculum or otherwise.

It is therefore a desired need to improve the state of the art of illuminators that are used in vaginal speculum assemblies and also to minimize at least some of the above stated problems confronted by the patient and caregiver in the use and operation of same.

SUMMARY OF THE INVENTION

According to one aspect, there is disclosed a speculum assembly comprising a speculum including a handle portion having a receiving cavity, a portable illuminator having a contained power source and an integrally contained light source that is selectively inserted into the handle portion. The portable illuminator is sized to fit at least partially within the receiving cavity, wherein the assembly further includes means for protecting the portable illuminator from contamination.

The protecting means can include, according to one embodiment, a disposable sheath member that is attached to at least a portion of the exterior of the illuminator. In one version, the sheath member covers substantially the entirety of the illuminator. In another version, the sheath member covers at least a portion of the illuminator that extends outwardly from the receiving cavity when the portable illuminator is inserted therein. The extending portion includes an outer profile that is larger than the outer profile of the handle portion of the speculum.

According to one aspect, a plurality of sheath members can be provided, the supply of sheath members being arranged in a stacked configuration to permit individual dispensing onto an illuminator.

The sheath members can include, according to one version, at least one portion, such as a window portion, made from a light transmissive material. According to yet another variation, the sheath member selectively permits only a portion of the light spectrum to pass therethrough or is treated to attenuate or otherwise to affect the distribution of light from the illuminator. The sheath member can be made from a transparent or, for example, a colored material to permit filtering of light transmitted by the illuminator.

The sheath member can further include at least one perforated tear strip member to enable removal from the illuminator, wherein the disposable sheath member covering the extending portion can be made from a semi-rigid plastic material and the sheath member that is configured to cover the entire illuminator is made from a highly flexible thin plastic film material.

According to another version, the portable illuminator comprises a housing that includes a projecting region that retains the portable light source and a pair of protective shoulders surrounding the projecting region. Preferably, each of the protective shoulders is contoured to facilitate cleaning thereof. The shoulders are further defined by a spacing into which a set of centering fingers of the speculum is fitted. The fingers and their engagement with the illuminator defines a predetermined distance that the illuminator can be inserted into the receiving cavity, thereby defining a gap between the nearest extending surface of the illuminator and the end of the handle portion. The gap permits the presence of a sheath member and further prevents the snagging of a glove or fingers when the illuminator is inserted in a speculum. In addition, the alignment between the centering fingers and the spacings of the illuminator insure optical alignment between the contained light source and a light pipe used to guide light to the patient.

The centering fingers are provided according to one version at the proximal end of a curved light pipe of the speculum. The proximal end of the light pipe is situated in the upper end of a handle portion of the speculum, the pipe further including a distal end that is provided along an axial portion of the speculum, such as a lower blade thereof. The facing surface of the distal end includes a contoured shape wherein light from the illuminator is directed and emitted. The contoured end preferably includes an optical finish, wherein the distal end includes a pair of lateral edges having radii less than or equal to 0.010 inches to improve light transmission and to reduce back reflection relative to a user of the speculum.

According to yet another version, a switch is provided on the exterior of the housing of the illuminator, wherein anti-pinch means are created to prevent pinching of a user's glove when operating the illuminator. According to one version, a recessed slot is provided into which the switch is disposed, the switch being a slide switch.

Preferably, the portable illuminator of the assembly is reusable and the speculum is disposable.

According to another aspect, there is provided a speculum assembly comprising a speculum including a handle portion having a receiving cavity, a portable illuminator having a contained light source that is inserted into the handle portion, the illuminator being sized to fit at least partially within the receiving cavity, and anti-pinch means for preventing pinching of a user's glove during insertion of the illuminator.

The anti-pinch means according to one version includes a gap that is defined between the portable illuminator and the speculum when the illuminator is inserted into the receiving cavity. The anti-pinch means permits the illuminator to be inserted to a predetermined distance into the receiving cavity, thereby creating the gap between the end of the handle portion and the nearest surface of an extending portion of the portable illuminator.

The exterior profile of the extending portion of the portable illuminator is larger than that of the exterior profile of the handle portion. Preferably, the gap defined is no less than about 0.020 inches.

According to another version, a disposable sheath member is provided that is sized to cover at least a portion of the exterior of the illuminator, the sheath member having a thickness that is smaller than that of the gap. The sheath member can cover the majority of the exterior of the illuminator in one version or can cover the portion of the illuminator that extends from the handle portion when the illuminator is attached, according to another version.

According to one version, the portable illuminator is insertable to only a predetermined distance within the receiving cavity, thereby defining a gap between the end of the handle portion and the nearest surface of an extending portion of the illuminator. The gap formed permits assembly of the illuminator to the handle portion without pinching of a user's glove. According to one version, the gap is no less than about 0.020 inches.

An advantage realized by the herein described assembly is a portable illuminator that can be fitted within and removed from the handle portion of a vaginal speculum without pinching or snagging of the user's glove.

Another advantage of the herein described assembly is that the portable illuminator and speculum include features to insure repeatable optical alignment between the light source of the illuminator and the light pipe of the speculum each time the illuminator is inserted into the speculum.

Yet other advantages realized by the present assembly are that the herein described illuminator is compact, durable, easy to clean and does not easily permit fluid ingress, readily enabling reuse. The illuminator is sufficiently durable to absorb significant impact and/or shock loads, such as those that can occur from dropping the illuminator when examining a patient. In addition, the illuminator includes features permitting the dissipation of generated heat from the contained light source and related circuitry, eliminating safety concerns and permitting the illuminator to be used independently, for example, as an examination light.

In addition, making the illuminator portable enables the assembly to be versatile, for example, in remote locations wherein the profile of the illuminator and the handle portion of the speculum are sufficiently compact to enable greater ease of use between patients, for example bed-ridden patients.

The speculum, as used herein with the portable illuminator, also produces improved light transmission relative to the target (e.g., the cervix) with reduced back reflection.

Additionally, the speculum is constructed to provide adequate heat dissipation irrespective of the form of illuminator received therein, the speculum for example, including a plurality of outer ribs on the handle portion that not only assist in conducting heat away from the patient, but also assist in material flow, the speculum in this instance being a plastic molded component.

These and other features and advantages will become readily apparent from the following Detailed Description which should be read in conjunction with the accompanying drawings.

BRIEF DESCRIPTION OF THE DRAWINGS

FIG. 2 is a bottom perspective view of the portable illuminator of FIG. 1;

FIG. 3 is a top perspective view of the portable illuminator of FIGS. 1 and 2;

FIG. 4 is a bottom perspective view of the portable illuminator, as attached to a handle portion of a vaginal speculum;

FIG. 8 is an enlarged bottom perspective view of the portable illuminator of FIG. 2;

FIG. 9(a) is a partial perspective view of an electrical device having an interface that is engageable with that of the portable illuminator of FIG. 8;

FIG. 9(b) is a partial view of the portable illuminator of FIGS. 1-3, as attached to an electrical device of FIG. 9(a), the latter being used to supplement and/or bypass the portable power source contained in the portable illuminator;

FIG. 17 is a side view of the charging station of FIGS. 15(a)-16, having a portable illuminator retained therein;

FIG. 18(a) is a partial perspective view of the distal end of the light pipe of the vaginal speculum of FIGS. 4-6(c) in accordance with one embodiment; and FIG. 18(b) is a partial side view of the vaginal speculum of FIGS. 4-6(c), including the light pipe thereof.

DETAILED DESCRIPTION

The following embodiment details the use of a portable illuminator as used with a vaginal speculum assembly wherein the illuminator can also be independently used as an examination light. Various terms are used throughout to provide a suitable frame of reference with regard to the accompanying drawings such as "lower", "upper", "top", "bottom", "within", "lateral", "upon", "front", "back", and the like. Such terms are not intended to be overly limiting, however, except where so specifically indicated.

Figure 1:
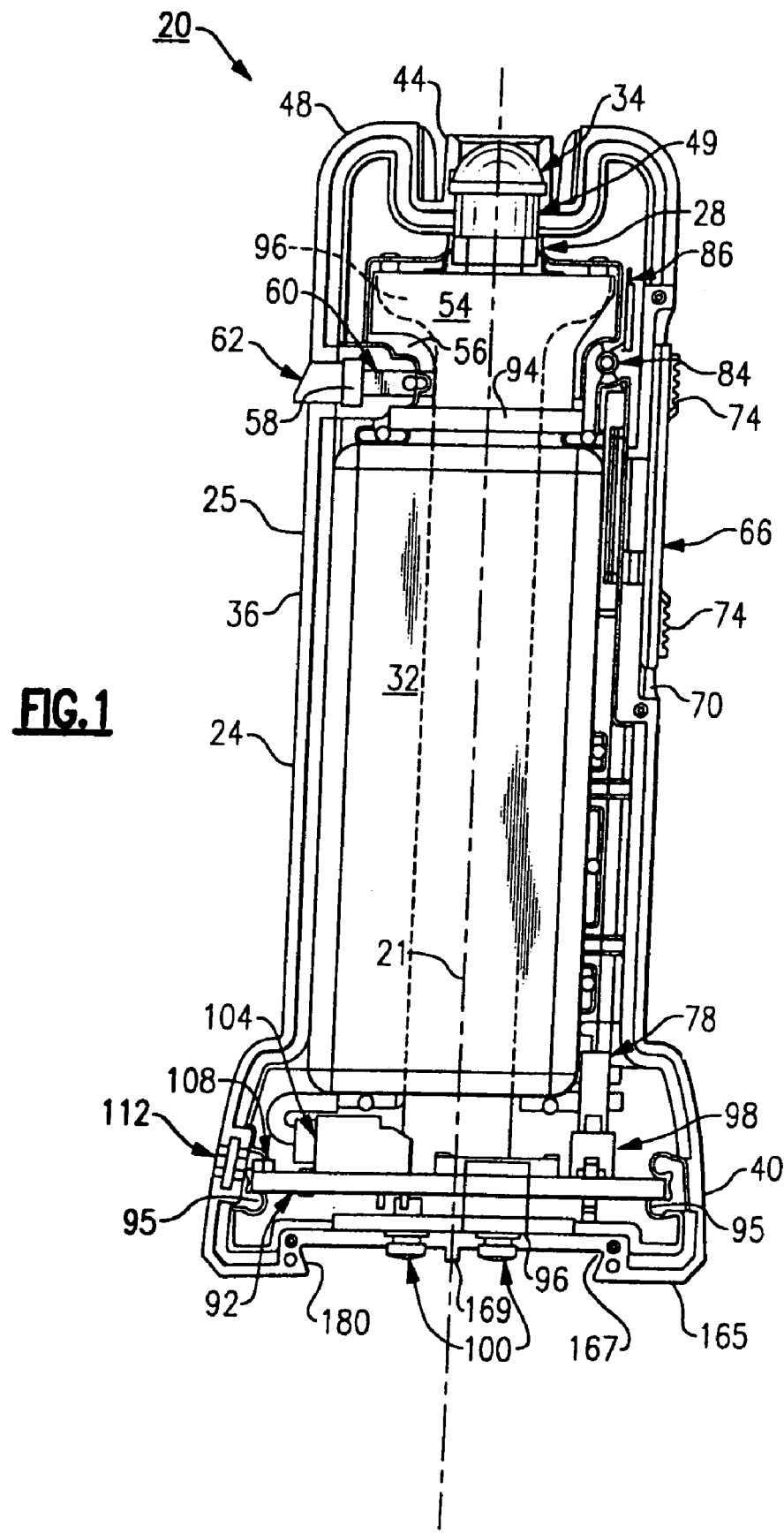
FIG. 1 is a side view of a portable illuminator, shown in section, made in accordance with an exemplary embodiment.

Referring to FIG. 1, there is shown a portable illuminator 20 that is defined by a housing or body section 24 having an interior sized to retain a number of components, including, among others, at least one portable light source and at least one portable power supply. According to the specific embodiment described herein, the portable light source is a white LED 28, such as, for example, those manufactured and sold by Nichia America, Inc. and Lumileds, Inc., while the portable power source includes at least one rechargeable battery 32, such as, for example, a Model UF612248PJFH lithium-ion battery manufactured by Sanyo Corp, the battery having suitable characteristics to sufficiently power the LED. Though the use of an LED is preferred, it should be noted that the design of the illuminator 20 is intended to make it "portable"; that is, such that it is not tethered and does not require a non-portable power source, such as a wall transformer or AC power supply, and wherein the illuminator functions as an integrated unit. To that end, it should be readily apparent that other forms of portable light sources, such as arc lamps and/or incandescent lamps, or other rechargeable power sources, such as other forms of batteries or alternative sources; such as, for example, capacitors capable of being recharged for portable use can be substituted.

According to this embodiment, the housing or body section 24 of the portable illuminator 20 is manufactured from a lightweight, durable material, such as a moldable plastic, and is further defined by an upper housing portion 36 and a lower base portion 40. The housing 24 according to the present embodiment is made from a two piece shell-like structure that is ultrasonically welded or otherwise connected together. Other forms of construction, however, should be readily apparent. For example and alternatively, a battery compartment could be provided having a removable cover (not shown), if desired, for removing and replacing the rechargeable battery 32 as needed.

The upper housing portion 36 is defined by a relatively flat, thin section having a substantially constant thickness and width wherein each of these dimensions approximately equals that of the contained battery 32. According to this embodiment, the lower base portion 40 is significantly wider than that of the upper housing portion 36, the former expanding from a minimum width adjacent the bottom of the upper housing portion to a maximum width at the bottom thereof. The transition from the top to the bottom of the lower base portion 40 is in the form of a substantially trapezoidal shape, as viewed from the side of the illuminator 20; see for example, FIG. 3. This transition provides an ergonomic design and further assists in positioning and retaining the illuminator 20 in a charging station 250, FIG. 17, as described in greater detail below.

The LED 28, according to this embodiment, is retained within a substantially cylindrical region 44 projecting from the top of the upper housing portion 36. The cylindrical region 44 preferably surrounds the lens envelope (not shown) of the LED 28, as well as a front lens element 34, wherein the cylindrical projecting region protects both the LED and lens element from shock and impact loads.

The LED 28 is further housed within a retaining structure 49 wherein the electrical contacts of the LED are attached to a flexible circuit assembly 96, one end portion of which covers a heat sink 54 made from aluminum or other material with suitable heat conductivity properties that is disposed between the battery 32 and the LED 28, each being disposed within the upper housing portion 36. The remainder of the flexible circuit assembly 96 extends downwardly across one facing side of the illuminator 20 to the bottom of the lower base portion 40. The electrical contacts (not shown) extending from the LED 28 are attached to the flex circuit assembly 96 using a thermal epoxy, such as Emerson Cuming Stycast 2850, such that the contacts also conduct heat away from the LED 28 to the heat sink 54.

The retaining structure 49 can include an interior reflective surface (not shown) to assist in directing light towards the front lens element 34. According to this embodiment, the heat sink 54 includes a lateral recess 56 that permits the inclusion of a retention pin 58 having a beveled end 62 that extends outwardly from one lateral side 25 of the housing 24. The beveled end 62 of the retention pin 58 is biased outwardly by means of a spring 60. According to this embodiment, a spacer 94, having a layer of a soft foam material provided on upper and lower facing sides thereof, is disposed between the bottom of the heat sink 54 and the battery 32, this spacer providing isolation from shock and impact loads being applied to the illuminator 20.

As noted, a flexible or flex circuit assembly 96 is provided in relation to the LED 28, an upper end portion of the flexible circuit assembly being folded about the heat sink 54 and extending along the interior wide side of the illuminator 20. On the lateral side 25, FIG. 2, opposite the beveled retention pin 58, a slide switch 66 is vertically arranged within a slotted area 70 such that the switch is mainly recessed and does not extend outwardly beyond the exterior of the lateral side with the exception of a pair of tabs 74 disposed at respective ends of the exterior surface of the switch.

The slide switch 66 is biased in an off position by means of a switch spring 78 attached to a leaf spring 86 extending along substantially the entire lateral side of the housing 24. The leaf spring 86 is formed into a bump onto which a dowel pin 84 is disposed. The lower end of the leaf spring 86 is attached to the switch spring 78, the switch spring being further disposed in relation to a tactile switch 98 that is attached to the printed circuit board 92. Downward movement of the slide switch 66 from the off position, such as by means of finger pressure against one of the tabs 74, causes corresponding movement of the leaf spring 86 sufficient to cause the switch spring 78 to be loaded into compression to engage the tactile switch 98 and engaging same, thereby completing the electrical connection between the LED 28 and the battery 32 and energizing the LED. Additional movement of the slide switch 66 overcomes the detent provided by the dowel pin 84 to hold the switch in an energized position. Heat that is generated by the LED 28 and the flexible circuit assembly is dissipated by the heat sink 54.

In addition, the lower base portion 40 further retains a printed circuit board 92 that is supported horizontally (i.e., perpendicular to the major dimension of the battery 32) and retained by a pair of channels 95. The lower end portion of the flexible circuit assembly 96 is disposed in overlaying relation over the bottom of the printed circuit board 92, this portion of the flexible circuit assembly including a pair of integral electrical contacts 100 that extend outwardly from the bottom of the housing 24. Providing each of the electrical contacts 100 integrally on the flexible circuit assembly provides savings in terms of the overall space envelope of the illuminator 20.

With regard to the components included on the printed circuit board 92, the contacts 100 employ a bi-polar diode bridge, thereby enabling the illuminator 20 to be oriented relative to a suitable interface in any one of a number of ways with regard to at least one electrical device, as described in greater detail in a later portion. Additionally, the circuit board 92 includes a power conversion means, for example, a buck-boost constant current LED driver, such as a Model LTC 3453UF; which drives the LED with substantially constant current over the useful voltage limits of the contained battery 32 (e.g., 4.2 volts for a charged battery, 2.4 volts for a nearly depleted battery). Other means can be alternatively provided. A battery connector 104 is also connected to the top surface of the printed circuit board 92 and the battery 32, wherein the circuit board 92 further includes a safety or protection circuit to prevent shorting and over charging of the contained battery 32, such as, for example, a Model UCC 3952-PW-1, manufactured by Texas Instruments, Inc. In addition to the above and according to this embodiment, a current charge limiter is also included that prevents the illuminator from being charged by an electrical device connected to the contacts 100 while the illuminator 20 is enabled. A low-battery LED assembly 108 is also attached to the printed circuit board 92, including a window 112, disposed in a lateral side of the lower base portion 40, to indicate to a user when the contained battery 32 is either charged or in need of charge, such as, for example, through flashing or a change in color of the LED, in a manner that is known in the field. For example, the low-battery LED assembly 108 can illuminate one color through the window 112 when 10 minutes of "on" time remains and a second color when 5 minutes of "on" time remains. It should be readily apparent that other similar configurations can be contemplated.

The upper housing portion 36 further includes a pair of upper shoulders 48 spaced evenly apart from the cylindrical projecting region 44 on opposing lateral sides thereof. Each of the shoulders 48 extends upwardly, according to this embodiment, such that the top surface of each shoulder is substantially coplanar with or slightly above the top of the cylindrical projecting region 44. The shoulders 48 therefore provide an additional means to protect the portable illuminator 20, and particularly the contained LED 28 and lens element 34, from impact and shock loads. By including the shoulders and the foam spacer 94, and based on the compact design of the herein described illuminator, the illuminator 20 can withstand drops from as high as 4 feet.

Figure 5:
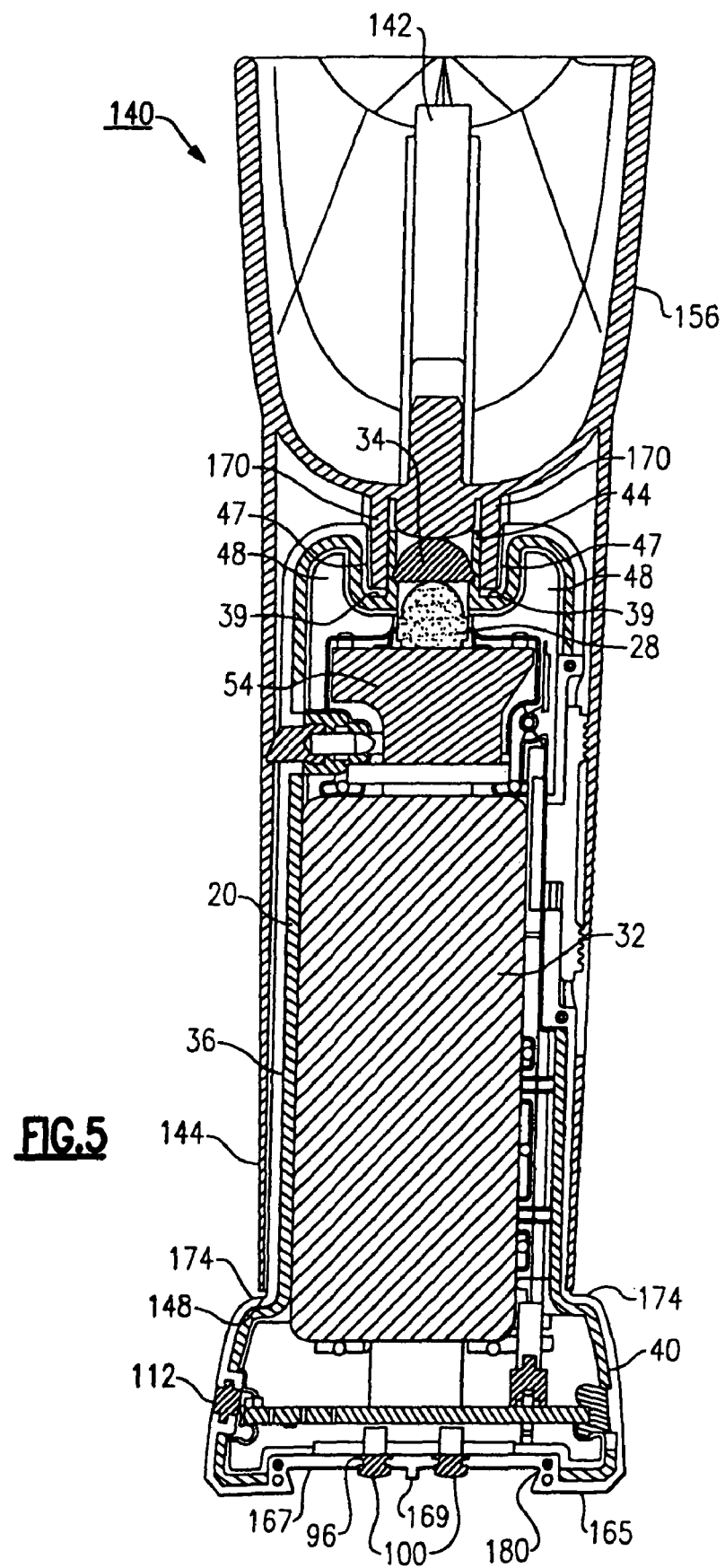
FIG. 5 is a sectioned elevational view of the vaginal speculum of FIG. 4 with the illuminator of FIGS. 1-3 inserted therein.

Referring to FIGS. 4 and 5, the upper housing portion 36 of the portable illuminator 20 is sized to be entirely fitted into the interior of a receiving cavity 148 of a handle portion 144 of a vaginal speculum 140. The contained LED 28 is optically coupled to a light pipe 142 having one end disposed in the proximal or upper end of the receiving cavity (not shown in FIG. 4, but shown more clearly in FIG. 18). Each of the upper housing and lower base portions 36, 40 are preferably contoured to facilitate cleaning, wherein the exterior profile of the lower base portion 40 is larger than that of the receiving cavity 148 of the vaginal speculum 140. When inserted into the receiving cavity 148, the window 112 is visible to a user.

Figure 6C:
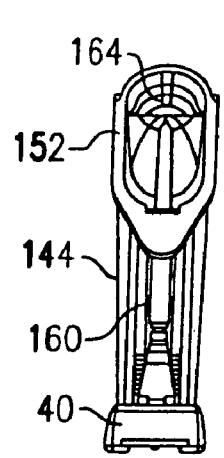
FIGS. 6(a), 6(b) and 6(c) are side, front and rear views, respectively, of the portable illuminator of FIGS. 1-3, as attached to a vaginal speculum.
Figure 6A:
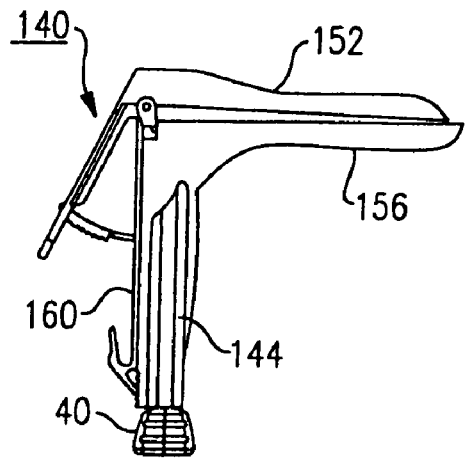
Figure 6B:
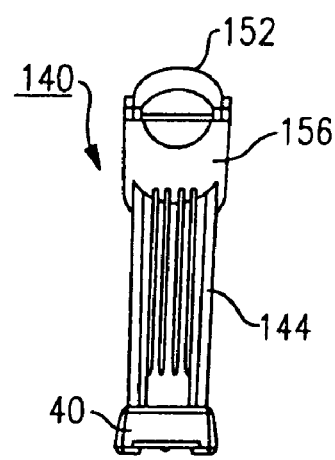

Referring briefly to FIGS. 5 and 6(*a*)-6(*c*), the vaginal speculum 140 used herewith is a disposable component that is manufactured preferably from an acrylic, polyamide or other suitable moldable plastic or other durable material. The speculum 140 is defined by an upper blade 152 and a lower blade 156 having the pistol-grip handle portion 144 that includes the receiving cavity 148. The rear of the upper blade 152 is attached to the upwardly extending fork of a yoke member 160 that is attached to the rear of the handle portion 144 of the speculum 140 to permit pivotal connection (angular articulation), as well as vertical elevation between the upper and lower blades 152, 156 in order to dilate the patient and provide an adequate viewing aperture 164 through the rear of the speculum 140.

Referring to FIGS. 18(*a*) and 18(*b*), the light pipe 142 is curved and extends from the upper end of the handle portion 144 along the interior of the lower blade 156. The proximal end 141 of the light pipe 142 includes a collecting lens 146 that is molded, according to this embodiment, as a center region in relation to a pedestal section contained within an annular gap formed between a set of centering fingers 170. At least one web or rib (not shown) is further provided to assist with moldability and to prevent the pedestal section from sagging about the collecting lens 146, the at least one rib improving material flow and gas removal around the lens. The purposes of the centering fingers 170 and collecting lens 146 with respect to an illuminator 20, FIG. 1, are discussed in greater detail in a succeeding portion of this description, wherein each provides improved optical coupling with the light source 28 of the portable illuminator 20.

The light pipe 142 receives light through the collecting lens 146 at the proximal end 141 and transmits light by means of internal reflection, wherein light is then emitted from the distal end 147. The distal end 147 of the light pipe 142 is preferably molded into the lower blade 156 of the speculum 140 and has a contoured configuration. By "contoured", what is meant is that the surface of the distal end has a defined shape that is not a 90 degree cut with respect to the axis of the light pipe 142. Therefore, it is intended that this term can cover both a range of angled surfaces, as well as curvi-linear surfaces, such as spherical, parabolic and the like. The contour of the distal end 147 is preferably formed as a scallop, such as would be cut by means of an end mill or similar apparatus. Alternatively, the above shape can be placed into the molding process for the lower blade 156 of the speculum 140, for example, if the speculum is being made from polystyrene, acrylic or other similar light transmissive materials.

The contour provided in the distal end 147 according to this particular embodiment is essentially a scalloped cut producing an inwardly (i.e., concave) curved portion or face having a radius of approximately 1.5 to 3.5 inches. The center of the radius is provided from a point Q, FIG. 18(*b*), which is approximately 2.6 inches, as measured distally from the rear or proximal side of the handle portion 144 and approximately 2.4 inches, as measured vertically from the top of the trough of the lower blade 156. These dimensions are shown in FIG. 18(*b*). It is noted that both dimensions locating the point Q for the herein described speculum 140 can be varied at least +/−0.030 inches and still produce a desirable effect. The herein described distal end 147 can alternatively be formed using an angled straight cut approximating that of the radiused scalloped end described above. According to one version, a suitable angle of approximately 70 degrees, as measured clockwise from the proximal upper end of the cut with respect to the perpendicular, FIG. 18(*b*), is provided, thereby creating a downwardly extending face. This angle can vary from approximately 55 degrees to approximately 80 degrees for purposes of providing improved illumination spot quality, while still reducing glare to the user. Each of the foregoing features is further described in greater detail in PCT Application No. PCT/US2006/12320, the entirety of which has previously been incorporated by reference. In addition to the foregoing, the herein described light pipe 142 includes a pair of lateral edges 149, which with respect to the sides of the radiused cut, are made essentially perpendicular to that of the face. Having relatively sharp edges 149 (i.e., radii less than or equal to 0.010 inches) provides an effective means of minimizing stray light. In addition and according to this embodiment, the face of the distal end 147 is polished and is also preferably treated with an optical finish, such as SP1 B1 to D3, in order further enhance light transmission.

In passing, it should be noted that the handle portion 146 of the herein described speculum 140 and the receiving cavity 148 are each sized to permit the selective inclusion of either a tethered illumination assembly or the portable illuminator 20. As such, the receiving cavity 148 includes features, for example, that require a tethered illumination assembly (not shown) to be insertable but only insertable in a single axial orientation that properly aligns the assembly with the collecting lens 146. More particularly, the receiving cavity 148 includes a pair of opposed rail-like portions formed between interior parallel sidewalls of the handle portion 144 and extending over substantially the length of the receiving cavity. These portions are used to align a tethered illumination assembly (not shown) and to allow the tethered assembly to be inserted into the handle portion 144 in either one of two 180 degree spaced rotational orientations. The rail-like portions also align with guide slots 37, FIGS., 2,3, formed on the exterior of the upper housing portion 36 of the portable illuminator 36 to allow the assembly to be mounted in either of two 180 degree spaced rotational orientations.

The handle portion 144 according to this version is wider than previous versions to enable the upper housing portion 36 of the portable illuminator 20 to be fitted therein. As such, this handle portion 144 is defined by a larger aspect (width/depth) ratio that is ergonomically superior as well as actually being stronger than previous known versions, allowing thinner walled construction to provide similar or greater strength characteristics. According to this embodiment, the aspect ratio is about 2:1, although a range of about 1.25:1 to 3:1 is suitable to provide adequate stability and greater rigidity, while permitting hand-held operation. In addition, the front facing side of the handle portion 144 includes a plurality of exterior ribs 143, FIG. 6(*b*), that provide additional heat dissipation with regard to a contained illumination assembly by keeping a user's fingers away from "hot" surfaces wherein these ribs also additionally aid in manufacturability of the speculum 140 by providing material. Details relating to the retention and other above-noted features of the receiving cavity 148 and speculum 140 are described in greater detail in PCT/US2006/12116, previously incorporated by reference herein.

Referring to FIGS. 1, 5 and 8, the bottom surface 165 of the portable illuminator 20 includes a recessed surface portion 167, defining an interface 166 that includes the pair of electrical contacts 100 extending outwardly therefrom. A transverse rib 169 is further provided between the pair of electrical contacts 100 in approximately the center of the bottom surface 165. A pair of side walls 180 defines the transition between the recessed surface portion 167 and the bottom or base surface 165 of the illuminator 20. Each of the side walls 180 is inwardly angled; that is, each side wall angles inwardly from the bottom surface 165 relative to the primary axis 21, FIG. 1, of the illuminator 20. In addition, each of the side walls 180 according to this embodiment further comprise a pair of angled segments 181, 182, FIG. 8, extending laterally outward relative to a centerline 168, FIG. 8, running perpendicular to the axis of the transverse rib 169.

The bottom surface 165 and the recessed surface portion 167 of the lower base portion 40 of the portable illuminator 20, as described herein, define an interface 166 that can accommodate various electrical devices, a first such electrical device 186 being shown by way of example in FIGS. 9(*a*) and 9(*b*). According to this embodiment, the device 186 is an auxiliary power module (partially shown) that includes a plug 184 having a mating interface 185 corresponding to that of the portable illuminator 20. The plug 184 is relatively compact and ergonomic in design and includes a pair of exposed electrical contacts 183 that engage the electrical contacts 100 of the illuminator interface 166, the plug further having a strain relief 188 extending to a cable 189 further extending to a power source (e.g., an AC power supply—not shown) used to supplement and/or bypass or replace the battery 32, FIG. 1, which typically acts as the primary power source of the illuminator 20, FIG. 1. The design of the herein plug 184 actually utilizes a center mechanical contact (not shown) that is disposed between the exposed electrical contacts 183 and within the interior of the plug 184. Each of the contacts is spring biased, wherein the center contact provides an interior positioner.

Referring more particularly to FIG. 9(*a*), the module plug 184 includes a pair of axially extending areas or portions 187 extending from an end surface 191. Each of the axially extending areas 187 includes interior lateral walls 193, each of the latter being defined by oppositely oriented angled surfaces 195, 197 in relation to a centerline 199 of the interface.

These angled surfaces 195, 197 engage with the oppositely oriented segments 181, 182 formed on the illuminator interface 166, each of which define respective dovetails on the illuminator 20 and plug 184 to allow engagement of the illuminator 20, FIGS. 8 and 9(b), from only one lateral direction relative to the auxiliary power module. Situated between the axially extending areas 187 and the electrical contacts 183 and centered therebetween are a pair of ribs 200 that upon assembly with the illuminator 20, surround the single transverse rib 169 of the illuminator 20, FIG. 9(b), in order to center the plug 184 of the auxiliary power module. The ribs 200 include an end wall or stop 201 that keeps the dovetail of the auxiliary power module plug 184 from jamming into the dovetail of the illuminator 20.

The illuminator interface 166 is adapted to also be attachable to other electrical devices, such as, for example, a charging station or base 250, FIGS. 15(a)-17, the station having contained circuitry used to charge the battery 32, FIG. 1, of the illuminator 20 without having to remove the battery from the housing 24, FIG. 1, through selective coupling with the herein defined interface.

More particularly and referring to FIGS. 15(a)-17, the charging station or base 250 is defined by a unitary assembly that is constructed from an upper section 251 and a lower section 252, respectively, the charging station further including a number of components, including a receptacle 253 and a printed circuit board 260 sandwiched therebetween. The receptacle 253 includes a receiving port 254 that extends through an opening 261 formed in the upper section 251 to permit the passage of an illuminator 20, FIG. 17. The receiving port 254 includes an inwardly tapering top opening 259, FIG. 15(b), wherein the receptacle 253 is defined by a rectilinear cross section having a series of lateral or side surfaces, as well as a bottom surface 257. The printed circuit board 260 is disposed between the bottom surface 257 of the receptacle 253 and the lower section 252, the circuit board containing a plurality of components, including a pair of power input pins 255 that extend through the bottom surface 257 of the receptacle 253 into the receiving port 254.

A pair of engagement arms 258 includes contoured or beveled shaped ends 262 that are each biased into a first position that extends into the interior of the receiving port 254. Each of the engagement arms 258 is pivotally attached to the lower section 252 and is movable between a first position and a second position when an illuminator 20 is inserted into the receiving port 254. The engagement arms 258 are internally biased into the first position by use of springs 266, each of the springs being housed within respective tubular members 270 made from noise suppression material. In addition, pads 271, made from a similar noise suppression material, are provided within the interior of lateral side surfaces of the receptacle 253 and act as stops with regard to each of the engagement arms 258. Fasteners 268 and 274 are used to secure the receptacle 253 to the upper section 251 and the upper section 251 to the lower section 252, respectively. In addition, another set of fasteners 272 is used to secure the printed circuit board 260 in place relative to the lower section 252. A set of contact pads 278 is used to cover openings in the bottom surface of the lower section 252 into which the fasteners 274 are inserted, enabling the charging station 250 to be evenly positioned on a horizontal surface (not shown).

As shown in FIG. 17, the lower base portion 40, FIG. 2, of the illuminator 20 is sized to be fitted into the receiving port 254 of the charging station 250. As the illuminator 20 is fitted therein, the beveled ends 262 are caused to move from the first position by engagement of the top of the beveled ends with the bottom of the lower base portion 40. As the remainder of the lower base portion 40 is pushed downwardly, the beveled ends 262 are caused to cam outwardly from the first position toward the second position. Once the top of the lower base portion 40 passes beneath the cammed beveled ends, there is no longer any force bearing upon the engagement arms 252 and the beveled ends are biased back toward the first position, thereby retaining the illuminator in place through the action of the beveled ends against the top of the lower base portion 40 and bringing the electrical contacts 100 and power input pins 255 into engagement. This engagement places pressure on the illuminator 20 to keep the illuminator upright and moreover to insure alignment for maintaining electrical connection with the charging station 250. Moreover and due to the geometry of the engagement arms 252 and of the lower base portion 40, the illumination assembly is self-orienting when fitted into the receiving port 254. The power input pins 255 of the charging station 250 are bi-polar according to this embodiment, therefore, the illuminator 20 can be positioned using either lateral orientation for charging. The illuminator 20 can be removed by pulling the upper housing portion 36 in an upward direction, wherein the tapering lower base portion 40 causes the beveled ends 262 to once again cam outwardly to the second position and allow the illuminator to be removed from the receiving port 254. The charging station 250 includes an exterior port (not shown) that permits connection to a power supply (not shown), as well as a charging LED 282 on an opposite lateral side thereof that indicates when charging of the battery 32, FIG. 1, contained within the illuminator 20 is complete. The LED 282, for example, can flash and/or change color, to indicate the status of charging. According to the present embodiment, the illuminator will not charge while it is operating; that is, the illuminator must be turned off before charging same for safety reasons.

Though the exemplary charging station 250 is shown with a single receiving port 253 and receptacle 254, it should be readily apparent that this device can include a plurality of receiving ports in order to accommodate a varied number of portable illuminators 20. Therefore, the illuminator 20, FIG. 1, can be recharged in any open port when indicated by the low-battery LED assembly 108, FIG. 1, as viewed through window 112, FIG. 1.

The illuminator and its interface therefore enables use of the illuminator as an independent portable examination light, as well as numerous applications, for example, with other medical devices. In addition, placing the electrical contacts 100 at the bottom of the illuminator interface 166, enables the contacts to remain clean when using the interface with either the auxiliary power module 186 and/or the charging station 250.

Figure 7A:
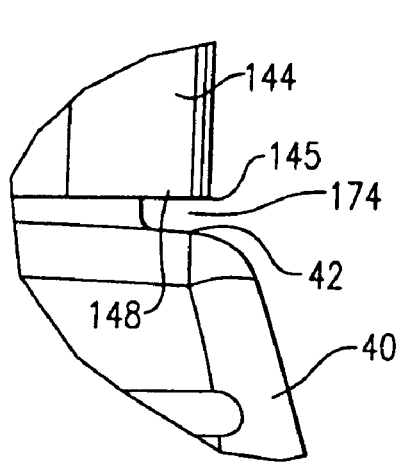
FIGS. 7(a) and 7(b) are enlarged views of FIGS. 6(a) and 6(b), respectively, illustrating a defined gap between an extending or lower base portion of the portable illuminator and the handle portion of the vaginal speculum.
Figure 7B:
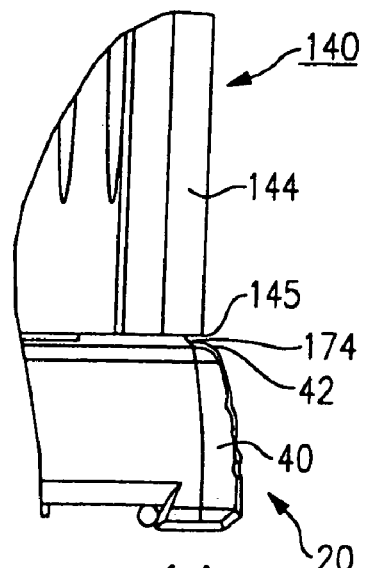

The following described aspects relate to the engagement of the portable illuminator 20 with the vaginal speculum 140. Referring to FIGS. 2 and 5, the shoulders 48 and the substantially cylindrical projecting region 44 of the portable illuminator 20 define respective lateral spacings 47 therebetween that are sized to accommodate the set of centering fingers 170, the latter also being depicted in FIG. 18(b), that extend downwardly (i.e., toward the open end) of the receiving cavity 148 of the speculum 140. The centering fingers 170 engage the spacings 47 when an illuminator 20 is inserted into the receiving cavity 148, wherein the fingers contact the top surface 39 of the upper housing portion 36, and permit the illuminator 20 to be inserted only to a predetermined distance. This engagement creates a gap 174 that is formed, as shown most particularly in FIGS. 7(a) and 7(b), between the nearest surface 42 of the extending lower base portion 40 and the end 145 of the handle portion 144. According to this embodiment, the defined gap 174 is no less than 0.020 inches.

In operation and when the portable illuminator 20 is inserted into the receiving cavity 148 of the speculum 140, the sliding switch 66 is automatically moved from the off position to a position that energizes the LED 28. In the meantime, the spring-loaded retention pin 58 provides a bearing force against the interior side wall of the receiving cavity 148 through its beveled end 62. This bearing force is sufficient to retain the illuminator 20 in place, but does not prevent removal of same from the receiving cavity 148 by a user. Additional details relating to this "automatic on" feature of the portable illuminator 20 and the retention of the illuminator in the receiving cavity 148 of the vaginal speculum 140 are described in co-pending Application No. PCT/US2006/12320, the entire contents of which are herein incorporated by reference.

Figure 10:
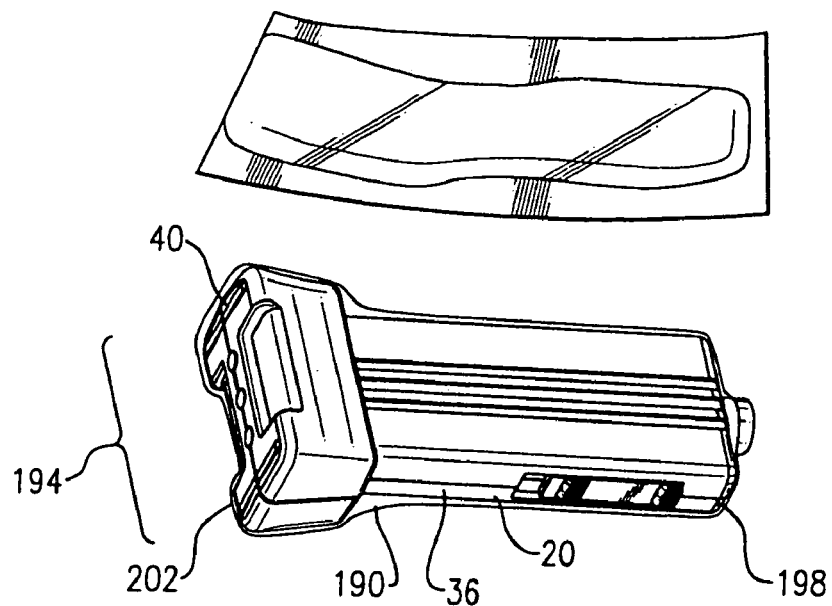
FIG. 10 is a perspective view of the portable illuminator of FIGS. 1-3 having a disposable sheath member according to a first design attached thereover.
Figure 11:
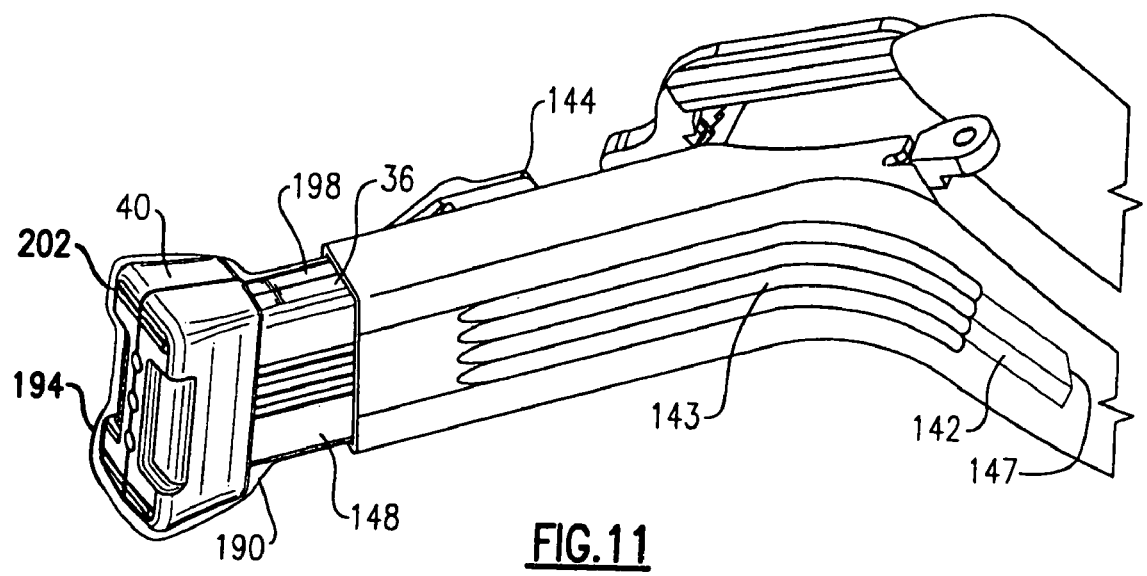
FIG. 11 is a perspective view of the illuminator with the attached sheath member of FIG. 10, as partially inserted into the receiving cavity of a vaginal speculum.
Figure 12:
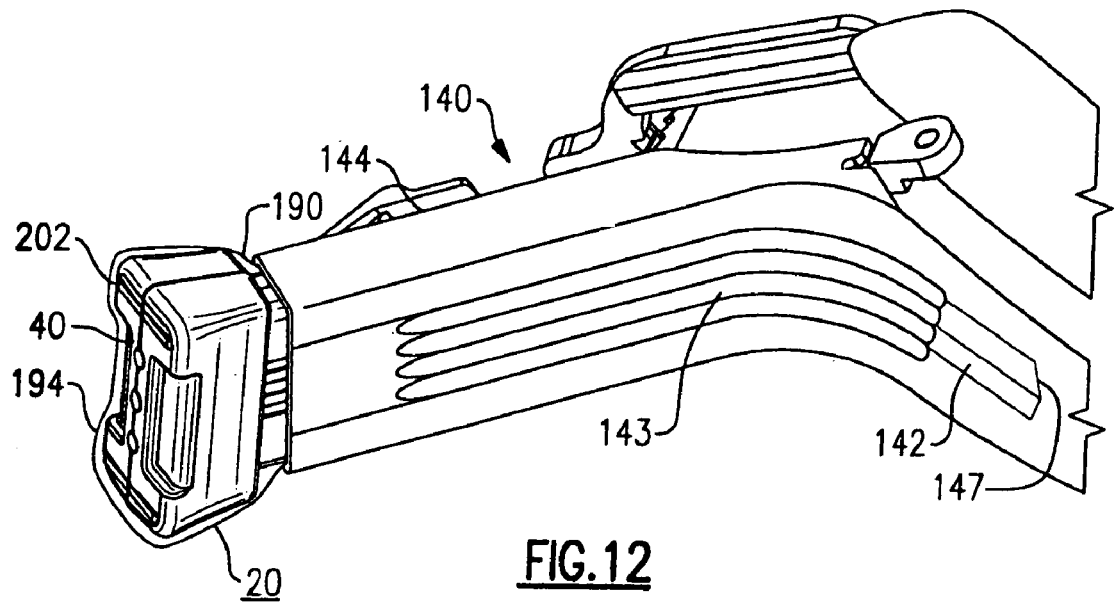
FIG. 12 is the perspective view of FIG. 11 with the portable illuminator and sheath member fully inserted into the receiving cavity.

Referring to FIGS. 11 and 12, the defined gap 174 permits the attachment of the herein described portable illuminator 20 relative to the receiving cavity 148 of the vaginal speculum 140, creates optical alignment (i.e., the proper axial spacing) between the contained light source and the light pipe, and further permits the attachment of a disposable sheath member 190. The sheath member 190 is preferably made from a thin film-like and highly flexible plastic material, such as polyethylene, that is wholly enclosed with the exception of an open lower end 194. The sheath member 190 according to this embodiment is defined by an upper portion 198 having a length and width dimension that is sized to entirely accommodate the upper housing portion 36 of the portable illuminator 20 and a lower portion 202 similarly sized to wholly enclose the lower base portion 40, as shown in FIGS. 10 and 11, wherein the illuminator 20 is placed into the highly flexible sheath member through the open lower end 194.

The portable illuminator 20 and attached sheath member 190 can then be inserted into the receiving cavity 148 of a vaginal speculum 140, as shown in FIG. 11 and FIG. 12, wherein each of the illuminator and attached sheath member is retained by corresponding features provided on the exterior of the illuminator and the interior of the receiving cavity. As in the instance when no sheath member is present, the sliding switch 66 is caused to automatically energize the contained LED 28 when the illuminator 20 is inserted to the predetermined position within the receiving cavity in that the slide switch is caused to move from the biased off position to an on or energized position. As previously noted, the switch 66 is spring biased and therefore removal of the portable illuminator 20 from the receiving cavity 148 will cause the switch to slide back to the biased off position. Additional details concerning this feature in accordance with one embodiment are described in previously incorporated PCT Patent Application No. PCT/US06/12320.

Due to the size of the defined gap 174, which as previously noted is at least 0.020 inches according to this embodiment, the disposable sheath member 190 can be used to protect the portable illuminator 20 from cross contamination, while still providing an anti-snagging feature with respect to a user's gloves (not shown) or fingers while inserting and removing the illuminator from the speculum 140. Similarly, the slide switch 66, due to its recessed position within the slot 70 of the illuminator 20, also provides a similar anti-pinch or anti-snag means in the event the portable illuminator is used independently as an examination light.

The sheath member 190 can be made entirely from a light transmissive material, such as clear polyethylene, or can include a window portion (not shown) in the upper portion thereof to permit light from the contained LED 28 to be transmitted without interference to the light pipe of the speculum 140. Alternatively, the sheath member 190 could be colored in order to filter the light transmitted by the illuminator 20 to the tissue or otherwise be treated in order to modify the characteristics of the transmitted light. This coloring or treatment would allow the caregiver to use the illuminator 20 without modification for varying the spectrum of the transmitted light, for attenuating the transmitted light, or for changing the geometric distribution of the transmitted light. One example of a varied spectrum is producing the effect of "red-free" illumination for cervical examinations. Alternatively and rather than including a colored sheath member to permit various light modification, the vaginal speculum, including the light pipe, can be tinted, for example, during the molding process thereof to achieve the same purpose with regard to light filtering and/or attenuation.

Figure 13:
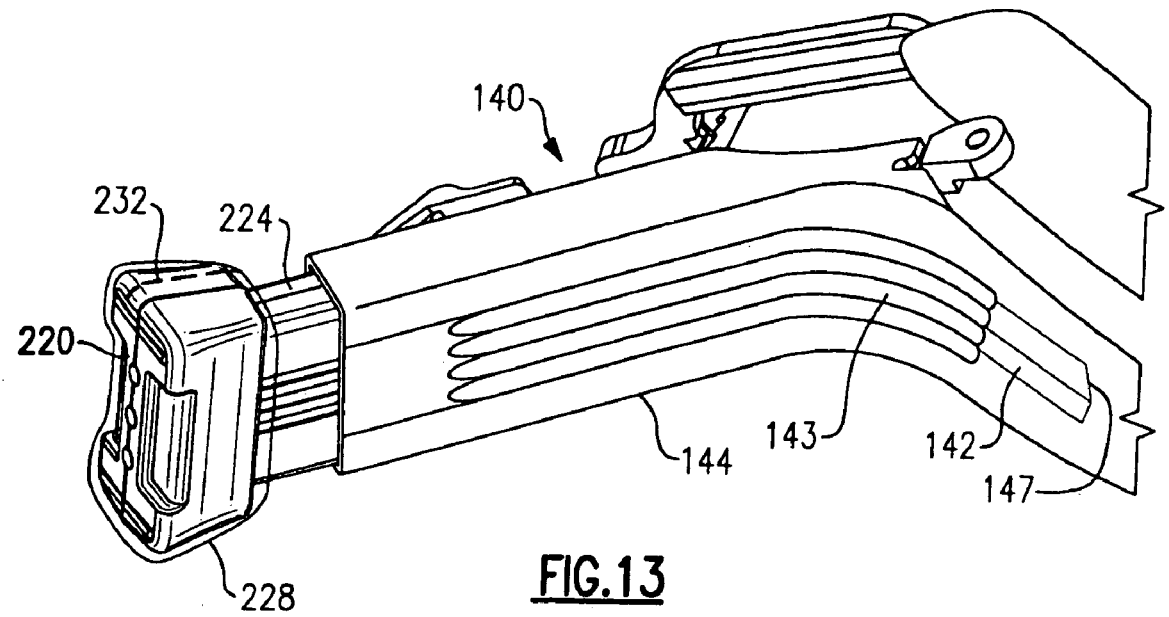
FIG. 13 is a perspective view of the portable illuminator of FIGS. 1-3 having a sheath member made in accordance with a second design that is attached over only an extending portion of a portable illuminator in relation to a vaginal speculum.

A second design of a disposable sheath member 220 is shown in FIG. 13. According to this embodiment, the sheath member 220 is sized to conform to only the lower base portion 40 of the portable illuminator 20. The sheath member 220 is made from a semi-rigid plastic material, such as polypropylene or polyethylene, and is defined by an open upper end 224 sized to conform with the tapered end of the lower base portion 40 of the illuminator 20, with the remainder of the sheath member having a substantially trapezoidal shape 228 that very closely conforms to and encloses the exterior of the lower base portion. When attached, the sheath member 220 is difficult to remove due to its close contacting fit with the lower base portion 40. Therefore, the sheath member 220 further includes at least one perforated tear strip 232 to enable release of same from the lower base portion 40 of the portable illuminator 20 when a patient examination is complete.

Figure 14:
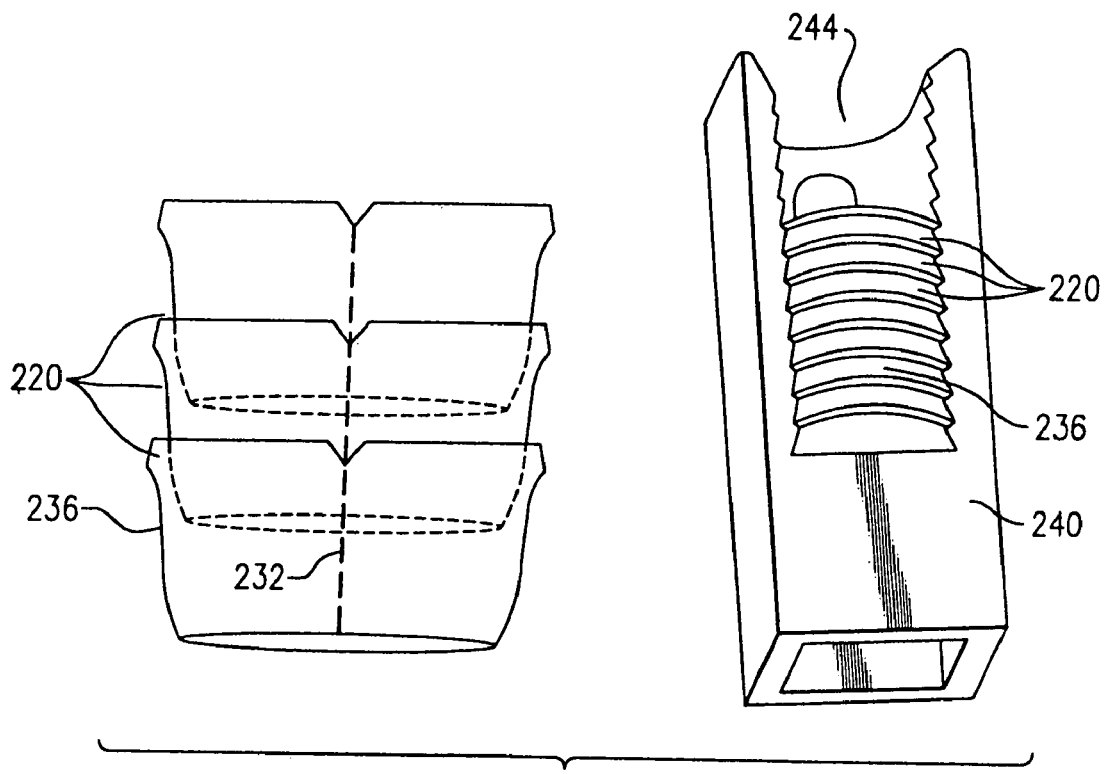
FIG. 14 depicts a stacked supply of the sheath members of FIG. 13 that can be dispensed individually onto a portable illuminator.
Figures 15A, 15B:
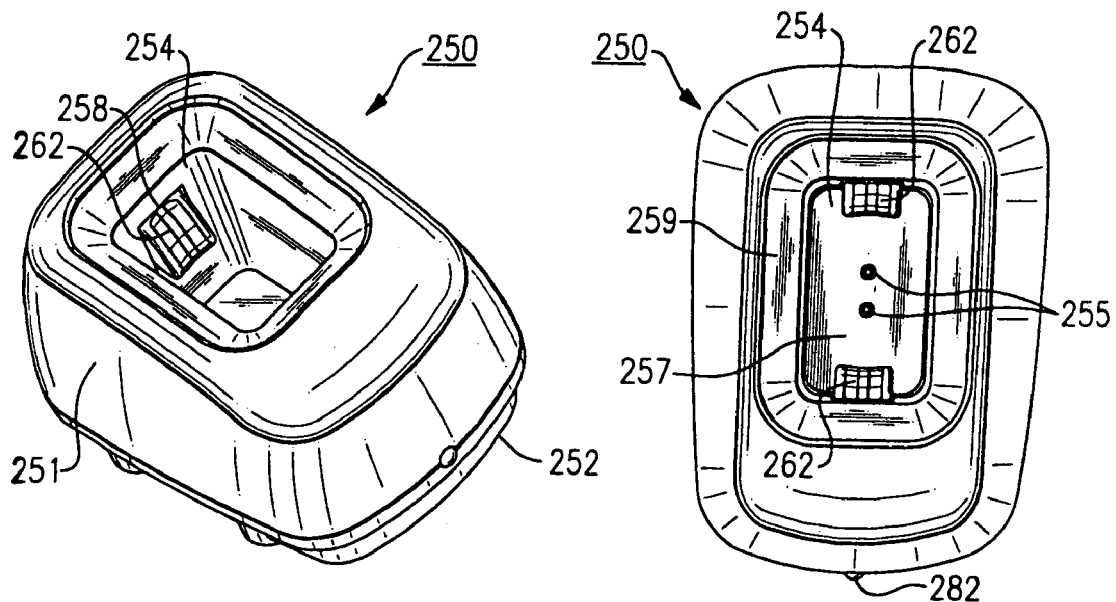
FIG. 15(a) is a top perspective view of a charging station used in connection with the portable illuminator of FIGS. 1-3.
FIG. 15(b) is a top plan view of the charging station of FIG. 15(a)
Figure 16:
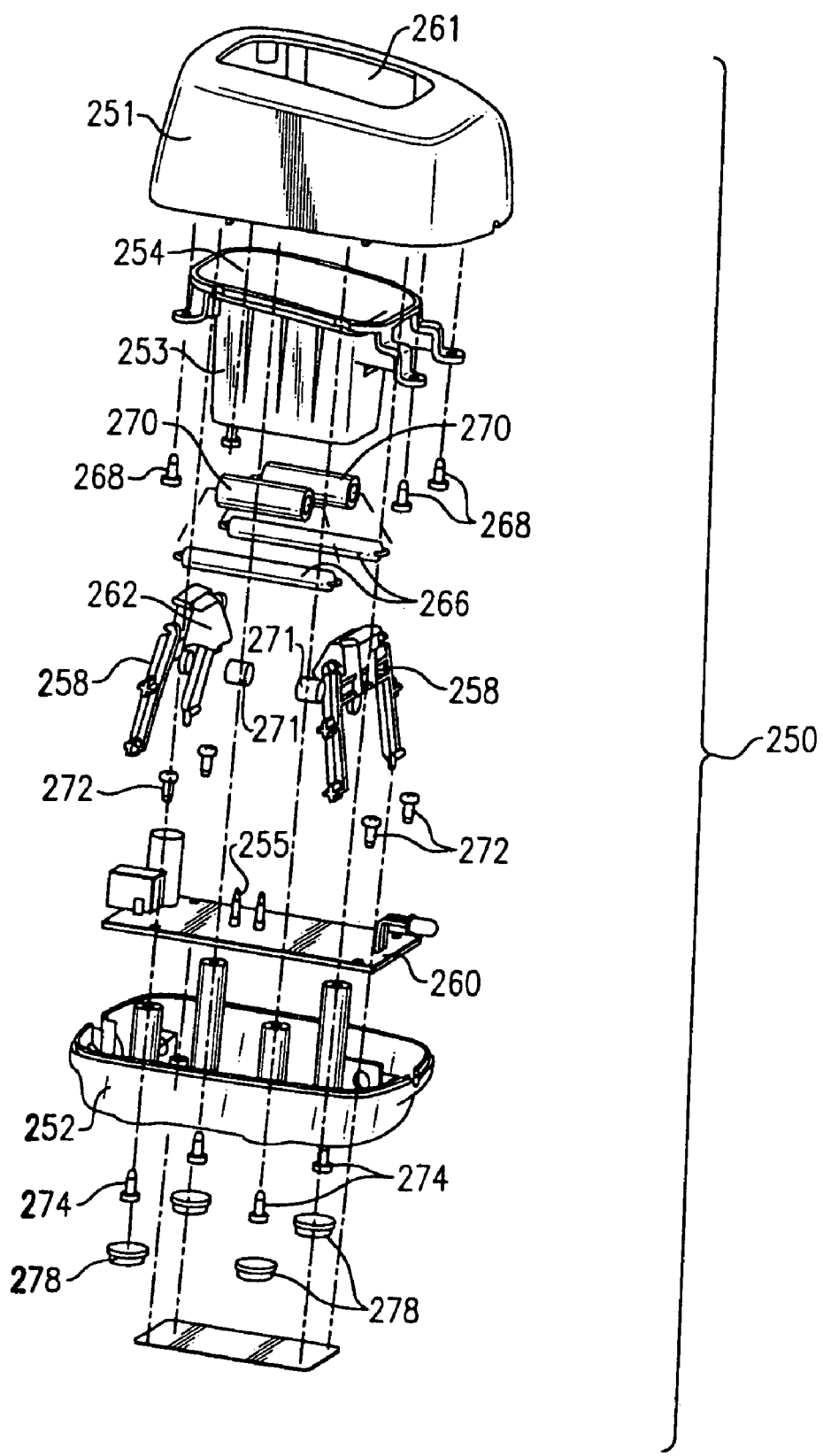
FIG. 16 is an exploded assembly view of the charging station of FIGS. 15(a) and (b)

Referring to FIG. 14, the sheath members 220, due to their shape and rigidity, can be arranged in a stacked configuration 236 and stored in a sheath supply container 240. The sheath supply container 240 is defined by a box-like structure that includes an open end 244 to permit individual dispensing of the sheath members 220, as needed. A sheath member 220 can be dispensed by sliding the upper housing portion 36 of a portable illuminator 20 through the open end 244 of the stacked configuration 236 within the supply container 240 and pushing the supply container downwardly such that a sheath member 220 is fitted over the lower base portion 40. The portable illuminator 20 can then be removed from the supply container 240 with a sheath member 220 being secured thereto.

PARTS LIST FOR FIGS. 1-18(b)

20 portable illuminator
21 primary axis, illuminator
24 housing or body section
25 lateral side
28 portable light source (LED)
32 portable power source (rechargeable battery)
34 front lens element
36 upper housing portion
37 guide slots
39 top surface
40 lower base portion
42 nearest surface
44 substantially cylindrical region
47 spacings
48 upper shoulders
49 retaining structure
54 heat sink
56 lateral recess
58 retention pin
60 spring, pin 62 beveled end
66 slide switch
70 slotted area
74 tabs
78 spring, switch
84 dowel pin
86 leaf spring
92 printed circuit board
94 foam spacer
95 channels
96 flexible circuit assembly
98 tactile switch
100 extending electrical contacts
104 battery connector
108 low battery LED assembly
112 window
140 speculum, vaginal
141 proximal end, light pipe
142 light pipe
143 exterior ribs
144 handle portion
145 end, handle portion
146 collecting lens
147 light emitting end, contoured
148 receiving cavity
149 lateral edges
152 upper blade
156 lower blade
160 yoke member
164 viewing aperture
165 bottom surface
166 interface, illuminator
167 recessed portions
168 centerline
169 transverse rib
170 fingers
174 gap
180 side walls
181 angled segment
182 angled segment
183 contacts, electrical
184 plug
185 mating interface
186 electrical device (auxiliary power module)
187 axially extending areas or portions
188 strain relief
189 cable
190 sheath member, disposable
191 end surface
193 interior lateral walls
194 open lower end
195 oppositely oriented angled surface
197 oppositely oriented angled surface
198 upper portion
199 centerline
200 ribs
201 end wall or stop
202 lower portion
220 sheath member, disposable
224 open upper end
228 trapezoidal shape
232 tear strip, perforated
236 stacked configuration
240 sheath supply container
244 open end
250 charging station or base
251 upper section
252 lower section
253 receptacle
254 receiving port
255 power input pins
257 bottom surface
258 engagement arms
259 tapered top opening
260 circuit board, printed
261 opening
262 beveled or contoured end
266 springs
268 fasteners
270 tubular members
271 pads
272 fasteners
274 fasteners
278 contact pads
282 charging LED It will be readily apparent that there are numerous modifications and variations to those skilled in the field that is possible within the intended nature and scope of the apparatus, as described herein. For example and though the preceding embodiment has been described in terms of a specific disposable speculum, it is anticipated that this component could be reusable. Alternatively still, the illuminator herein described could be used in conjunction with other medical diagnostic instruments, for example, such as a laryngoscope, an anoscope, or other device. The illuminator can also be used independently as an examination light, using the herein described electrical interfaces to supplement, replace and/or recharge the power source of the illuminator.

In addition and though the exemplary embodiment is made in terms of a disposable speculum, it is anticipated that the illuminator and interface described herein could also be commonly used with a reusable (e.g., metal) speculum. In another instance, for example, the light pipe described herein could be separably attached to the interior of a metal speculum and the illuminator could be attached thereto to illuminate a medical target (e.g., the cervix).

The invention claimed is:

1. A speculum assembly comprising:
a speculum including a blade portion insertable into a vagina and a handle portion having an open-ended receiving cavity, said receiving cavity being entirely enclosed except for said open end;
a removable illuminator having an integral power source and an integral light source, both disposed within an illuminator housing, said illuminator being sized to releasably fit at least partially within said open-ended receiving cavity of the handle portion; and
means for protecting said illuminator from patient contamination when said illuminator is fitted in said receiving cavity.

2. An assembly as recited in claim 1, wherein said protecting means includes a disposable sheath member that covers at least a portion of the exterior of said illuminator.

3. An assembly as recited in claim 2, wherein said disposable sheath member covers substantially the entirety of the exterior of the illuminator housing.

4. An assembly as recited in claim 3, wherein said disposable sheath member includes at least one window portion made from a light transmissive material.

5. An assembly as recited in claim 3, wherein said disposable sheath member is at least partially formed from a light transmissive material.

6. An assembly as recited in claim 3, wherein said disposable sheath member selectively passes only a portion of the light spectrum therethrough.

7. An assembly as recited in claim 3, wherein said disposable sheath member is made from a colored material.

8. An assembly as recited in claim 2, wherein said disposable sheath member covers at least an exterior extending portion of the illuminator, said disposable sheath member extending from said open-ended receiving cavity when said illuminator is inserted therein, wherein said exterior extending portion of said illuminator is defined by an outer profile that is larger than that of the outer profile of the handle portion of said speculum.

9. An assembly as recited in claim 8, wherein said illuminator housing is insertable only to a predetermined distance within said receiving cavity, thereby defining a gap between the end of said handle portion and the nearest surface of said extending portion of said illuminator.

10. An assembly as recited in claim 9, wherein said defined gap is formed irrespective of whether said illuminator includes said sheath member.

11. An assembly as recited in claim 9, wherein said defined gap permits assembly of said illuminator to said handle portion of said speculum without pinching of a user's glove between the illuminator and said handle portion.

12. An assembly as recited in claim 9, wherein said gap is no less than approximately 0.020 inches.

13. An assembly as recited in claim 8, including a plurality of said disposable sheath members that are disposed in a stacked configuration to permit dispensing thereof.

14. An assembly as recited in claim 13, wherein said plurality of disposable sheath members are disposed in a sheath member supply, said supply being configured to permit individual dispensing of said stacked sheath members relative to at least one illuminator.

15. An assembly as recited in claim 8, wherein said disposable sheath member includes at least one perforated tear strip to enable removal of said sheath member from said illuminator.

16. An assembly as recited in claim 2, wherein said disposable sheath member is made from a highly flexible material.

17. An assembly as recited in claim 2, wherein said disposable sheath member is made from a semi-rigid plastic material.

18. An assembly as recited in claim 1, wherein said illuminator housing includes a substantially cylindrical projecting region within which said light source is disposed, and a pair of protective shoulders surrounding said cylindrical projecting region.

19. An assembly as recited in claim 18, wherein each of said protective shoulders is contoured.

20. An assembly as recited in claim 18, including a switch formed on the exterior of said illuminator housing, said housing including a slot through which said switch is disposed, said switch being a slide switch configured to prevent pinching of a user's glove engaging said switch in the use of said illuminator.

21. An assembly as recited in claim 1, wherein said illuminator housing includes a portion that extends from said handle portion when said illuminator is inserted into said receiving cavity, said extending portion being contoured to facilitate cleaning thereof.

22. An assembly as recited in claim 1, wherein said illuminator is reusable.

23. An assembly as recited in claim 1, wherein said speculum is disposable.

24. A speculum assembly comprising:
a speculum including a blade portion insertable into a vagina and a handle portion having a receiving cavity, said receiving cavity being fully enclosed with the exception of an open end at the lower end of said handle portion;
a removable illuminator having an integral light source and an integral power supply, both disposed within an illuminator housing, said illuminator housing being sized to releasably fit at least partially within said receiving cavity of the handle portion; and
anti-pinch means for preventing pinching of a user's glove during use of said assembly.

25. An assembly as recited in claim 24, wherein said illuminator housing and said speculum include features such that when said illuminator housing is inserted into said receiving cavity, a gap between the lower end of said handle portion and the nearest surface of an extending portion of said illuminator is created, said gap providing said anti-pinch means.

26. An assembly as recited in claim 25, wherein the exterior profile of said extending portion of said illuminator is larger than the exterior profile of said handle portion.

27. An assembly as recited in claim 25, wherein said gap is no less than approximately 0.020 inches.

28. An assembly as recited in claim 25, including a disposable sheath member sized to cover at least a portion of said illuminator, said sheath member having a thickness which is smaller than said gap.

29. An assembly as recited in claim 28, wherein said sheath member covers the majority of the exterior of said illuminator.

30. An assembly as recited in claim 25, including a sheath member sized to cover the extending portion of said illuminator.

31. An assembly as recited in claim 25, wherein said illuminator includes a housing having a substantially cylindrical projecting region that includes said contained light source and a pair of spaced protective shoulders.

32. An assembly as recited in claim 31, wherein said speculum includes fingers sized to fit in spacings defined between said protective shoulders and said cylindrical projecting region when said illuminator is inserted in said receiving cavity.

33. An assembly as recited in claim 32, wherein said fingers engage said housing within said spacings and engage against the exterior of said housing, thereby defining said gap.

34. An assembly as recited in claim 32, wherein said fingers provide alignment for said illuminator in relation to a light pipe of said speculum, wherein engagement of said illuminator using said fingers within said spacings optically aligns said light source with said light pipe.

35. An assembly as recited in claim 34, wherein said light pipe includes a proximal end to which said illuminator is optically coupled and a distal end, said distal end being contoured.

36. An assembly as recited in claim 35, wherein said contoured distal end is provided with an optical finish.

37. An assembly as recited in claim 35, wherein said contoured distal end of said light pipe includes lateral edges having radii less than 0.010 inches.

38. An assembly as recited in claim 24, wherein said illuminator a housing includes a switch to selectively energize said contained light source, said anti-pinch means including a slot formed in the exterior of said housing into which said switch is disposed, such that an engageable portion of said switch is situated within said slot.

* * * * *